(12) United States Patent
Ebright et al.

(10) Patent No.: US 11,572,337 B2
(45) Date of Patent: Feb. 7, 2023

(54) ANTIBACTERIAL AGENTS: ARYLALKYLCARBOXAMIDO PHLOROGLUCINOLS

(71) Applicant: Rutgers, The State University of New Jersey, New Brunswick, NJ (US)

(72) Inventors: Richard H. Ebright, New Brunswick, NJ (US); Yon W. Ebright, New Brunswick, NJ (US); Joel S. Freundlich, New Brunswick, NJ (US); Ricardo Gallardo-Macias, New Brunswick, NJ (US); Shao-Gang Li, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/978,135

(22) PCT Filed: Mar. 6, 2019

(86) PCT No.: PCT/US2019/021004
§ 371 (c)(1),
(2) Date: Sep. 3, 2020

(87) PCT Pub. No.: WO2019/173507
PCT Pub. Date: Sep. 12, 2019

(65) Prior Publication Data
US 2021/0017126 A1     Jan. 21, 2021

Related U.S. Application Data

(60) Provisional application No. 62/639,352, filed on Mar. 6, 2018.

(51) Int. Cl.
| | |
|---|---|
| *C07C 235/60* | (2006.01) |
| *C07D 239/34* | (2006.01) |
| *C07D 213/65* | (2006.01) |
| *C07D 213/56* | (2006.01) |
| *A61P 31/04* | (2006.01) |
| *A01N 43/54* | (2006.01) |
| *A01N 43/40* | (2006.01) |
| *A01N 37/44* | (2006.01) |
| *C07D 213/30* | (2006.01) |
| *C07D 213/68* | (2006.01) |
| *C07D 295/096* | (2006.01) |

(52) U.S. Cl.
CPC ............ *C07C 235/60* (2013.01); *A01N 43/40* (2013.01); *A01N 43/54* (2013.01); *A61P 31/04* (2018.01); *C07D 213/30* (2013.01); *C07D 213/65* (2013.01); *C07D 213/68* (2013.01); *C07D 239/34* (2013.01); *C07D 295/096* (2013.01); *C07C 2601/02* (2017.05); *C07C 2601/16* (2017.05)

(58) Field of Classification Search
None
See application file for complete search history.

(56) References Cited

U.S. PATENT DOCUMENTS

| | | |
|---|---|---|
| 2,898,374 A | 8/1959 | Riedl |
| 4,061,769 A | 12/1977 | Ohno et al. |
| 4,421,763 A | 12/1983 | Hamano et al. |
| 5,411,728 A | 5/1995 | Jou et al. |

(Continued)

FOREIGN PATENT DOCUMENTS

| | | |
|---|---|---|
| CN | 105085219 A | 11/2015 |
| EP | 1764363 A2 | 3/2007 |

(Continued)

OTHER PUBLICATIONS

Grant & Hackh's Chemical Dictionary (5th Ed. 1987) at p. 148.*
Andre, et al., "Novel synthetic molecules targeting the bacterial RNA polymerase assembly", Journal of Antimicrobial Chemotherapy, 57, 245-251 (2006).

(Continued)

*Primary Examiner* — Po-Chih Chen
(74) *Attorney, Agent, or Firm* — Viksnins Harris Padys Malen LLP

(57) ABSTRACT

The invention provides compounds of formula (I) or (II) and tautomers and salts thereof, wherein variables are as described in the specification, as well as compositions comprising a compound of formula (I) or (II) or a tautomer or salt thereof, methods of making a compound of formula (I) or (II) or a tautomer or salt thereof, and methods of using a compound of formula (I) or (II) or a tautomer or salt thereof as, e.g., inhibitors of bacterial RNA polymerase or as antibacterial agents.

6 Claims, No Drawings

(56) References Cited

U.S. PATENT DOCUMENTS

| | | | |
|---|---|---|---|
| 6,022,983 | A | 2/2000 | Wuonola et al. |
| 6,169,181 | B1 | 1/2001 | Romines et al. |
| 6,191,288 | B1 | 2/2001 | Ramamoorthy |
| 6,228,882 | B1 | 5/2001 | Wuonola et al. |
| 8,114,583 | B2 | 2/2012 | Ebright et al. |
| 8,772,332 | B2 | 7/2014 | Ebright et al. |
| 9,133,155 | B2 | 9/2015 | Ebright et al. |
| 9,187,446 | B2 | 11/2015 | Ebright et al. |
| 9,315,494 | B2 | 4/2016 | Moslin et al. |
| 9,315,495 | B2 | 4/2016 | Ebright et al. |
| 9,517,994 | B2 | 12/2016 | Ebright et al. |
| 9,592,221 | B2 | 3/2017 | Ebright et al. |
| 9,595,221 | B2 | 3/2017 | Hamer et al. |
| 10,450,292 | B2 | 10/2019 | Ebright et al. |
| 10,800,725 | B2 | 10/2020 | Ebright et al. |
| 2003/0065039 | A1 | 4/2003 | Kharazmi et al. |
| 2005/0187170 | A1 | 8/2005 | Bantia et al. |
| 2006/0100291 | A1 | 5/2006 | Perry et al. |
| 2006/0246479 | A1 | 11/2006 | Ebright |
| 2007/0292355 | A1 | 12/2007 | Tamarkin et al. |
| 2008/0039511 | A1 | 2/2008 | Takemura et al. |
| 2013/0196050 | A1* | 8/2013 | Amino ............ A23L 27/204 426/650 |
| 2013/0237595 | A1 | 9/2013 | Ebright et al. |
| 2013/0289128 | A1 | 10/2013 | Ebright et al. |
| 2013/0296421 | A1 | 11/2013 | Ebright et al. |
| 2014/0073688 | A1 | 3/2014 | Pfarr et al. |
| 2015/0011647 | A1 | 1/2015 | Ebright et al. |
| 2015/0031640 | A1 | 1/2015 | Ebright et al. |
| 2015/0051275 | A1 | 2/2015 | Ebright et al. |
| 2015/0197512 | A1 | 7/2015 | Ebright et al. |
| 2016/0263083 | A1 | 9/2016 | Ebright et al. |
| 2021/0002246 | A1 | 1/2021 | Ebright et al. |
| 2021/0002266 | A1 | 1/2021 | Ebright et al. |

FOREIGN PATENT DOCUMENTS

| | | |
|---|---|---|
| JP | H09301915 A | 11/1997 |
| WO | 1998052899 | 11/1998 |
| WO | 2007094799 | 8/2007 |
| WO | 2012033846 | 3/2012 |
| WO | 2012037508 | 3/2012 |
| WO | 2013103969 | 7/2013 |
| WO | 2013119564 | 8/2013 |
| WO | 2013142812 | 9/2013 |
| WO | 2013192352 | 12/2013 |
| WO | 2014090875 | 6/2014 |
| WO | 2015120320 | 8/2015 |
| WO | 2017100645 | 6/2017 |
| WO | 2019160873 | 8/2019 |
| WO | 2019160875 | 8/2019 |

OTHER PUBLICATIONS

Batt, D, et al., "2'-Substituted chaicone derivatives as inhibitors of interleukin-1 biosynthesis", J Med Chem 36, 1434-1442 (1993).

Belogurov, et al., "Transcription inactivation through local refolding of the RNA polymerase structure", Nature 457 (7227), 332-335 (2009).

Boccard, J, et al., "A 3D linear solvation energy model to quantify the affinity of flavonoid derivatives toward P-glycoprotein", European Journal of Pharmaceutical Sciences 36, 254-264 (2009).

Bois, F, et al., "Halogenated Chaicones with High-Affinity Binding to P-Glycoprotein: Potential Modulators of Multidrug Resistance", J Med Chem 41, 4161-4164 (1998).

Bois, F, et al., "Synthesis and biological activity of 4-alkoxy chaicones: potential hydrophobic modulators of P-glycoprotein-mediated multidrug resistance", Bioorganic & Medicinal Chemistry 7, 2691-2695 (1999).

Bu, X, et al., "Synthesis of Exiguaflavanone K and (±)-Leachianone G", J Nat Prod 59, 968-969 (1996).

Chatterjee, et al., "Isolation and structure of archangelenone. Flavonoid constituent of Angelica archangelica", XP002692911, Database Caplus [Online] Chemical Abstracts accession No. 1973:489536.

Chopra, I., "Bacterial RNA polymerase: a promising target for the discovery of new antimicrobial agents", Curr. Opin. Investig. Drugs 8, 600-607 (2007).

Darst, "New inhibitors targeting bacterial RNA polymerase", Trends Biochem. Sci. 29 (4), 159-162 (2004).

Dong, X, et al., "Design, Synthesis, and Biological Evaluation of Prenylated Chaicones as Vasorelaxant Agents", Arch Pharm Chem Life Sci 342, 428-432 (2009).

Dong, X, et al., "Identification of SVM-based classification model, synthesis and evaluation of prenylated flavonoids as vasorelaxant agents", Bioorganic & Medicinal Chemistry 16, 8151-8160 (2008).

Doundoulakis, et al., "Myxopyronin B analogs as inhibitors of RNA polymerase, synthesis and biological evaluation", Bioorganic and Medicinal Chemistry Letters, vol. 14 (22), 5667-5672 (2004).

Doundoulakis, et al., "Myxopyronin B analogs as inhibitors of RNA polymerase, synthesis and biological evaluation", HCAPLUS Accession No. 2004:863124, 5 pages, Bioorganic & Medicinal Chemistry Letters, 14(22), 5667-5672 (2004).

Heron, M., et al., "Deaths: Final Data for 2006", National Vital Statistics Reports, vol. 57 (14), 135 pages (Apr. 17, 2009).

Ho, et al., "Structures of RNA polymerase-antibiotic complexes", Curr. Opin. Structl. Biol. 19, 715-723 (2009).

Honda, I, et al., "Structure-Activity Relationship of-Nitro-2,4,6-tri-hydroxybenzamide Derivatives in Photosynthetic Electron Transport Inhibition", Agricultural and Biological Chemi, Agricultural Chemical Society of Japan 54(5), 1227-1233 (1990).

Hu, "Total syntheses of biologically active natural products: motuporin, oleandolide, (±) -myxopyronin A and B", HCAPLUS Accession No. 2000:514322, 1 page, Diss. Abstr. Int., B 2000, 60(10), 5094.

Iinuma, M, et al., "Structure-Activity Correlation of Flavonoids for Inhibition of Bovine Lens Aldose Reductase", Chem Pharm Bull 37(7), 1813-1815 (1989).

Klevins, R, et al., "Estimating health care-associated infections and deaths in U.S. hospitals, 2002", Public Health Reports 122, 160-166 (2007).

Lin, W, et al., "Structural Basis of *Mycobacterium tuberculosis* Transcription and Transcription Inhibition", Molecular Cell 66(2), 169-179 (2017).

Lira, R., et al., "Syntheses of novel myxopyronin B analogs as potential inhibitors of bacterial RNA polymerase", Bioorganic & Medicinal Chemistry Letters 17(24), 6797-6800 (2007).

Mapunya, M, et al., "Tyrosinase activity of *Greyia flanaganii* (Bolus) constituents", Phytomedicine 18, 1006-1012 (2011).

Mukhopadhyay, et al., "The RNA polymerase "switch region" is a target for inhibitors", Cell 135, 295-307 (2008).

Mukhopadhyay, et al., "The RNA polymerase "switch region" is a target for inhbitiors", HCAPLUS Accession No. 2008:1312023, 2 pages, Cell 135(2), 295-307 (2008).

Patent Cooperation Treaty, International Searching Authority, Search Report and Written Opinion for PCT/US2019/021004, 13 pages, dated May 10, 2019.

Pubchem, "Chembl487037", CID 44562517, U.S. National Library of Medicine, p. 1-12 (2010).

Scott, R, et al., "The Direct Medical costs of Healthcare-Associated Infections in U.S. Hospitals and the Benefits of Prevention", Public Health Reports, 122, 160-166, Center for Disease Control and Prevention, 16 pages (2009).

Srivastava, et al., "New Target for inhibition of bacterial RNA polymerase: switch region", Curr. Opini. Microbiol. 14, 532-543 (2011).

Sun, L, et al., "Synthesis and Biological Evaluation of 2,4, 6-Trihydroxychalcone Derivatives as Novel Protein Tyrosine Phosphatase 1B Inhibitors", Chem Biol Drug Des 80, 584-590 (2012).

Villain-Guillot, et al., "Progress in targeting bacterial transcription", Drug Discov. Today 12 (5/6), 200-208 (2007).

Werner, S, et al., "Synthesis of non-natural flavanones and dihydrochalcones in metabolically engineered yeast", Journal of Molecular Catalysis B: Enzymatic 66, 257-263 (2010).

(56) References Cited

OTHER PUBLICATIONS

World Health Organization, "The Global Burden of Disease—2004 Update", World Health Organization, Geneva, ISBN 978 92 4 156371 0, 160 pages (2008).

Zhao, L., et al., "Synthesis and evaluation of antiplatelet activity of trihydroxychalcone derivatives", Bioorganic & Medicinal Chemistry Letters 15, 5027-5029 (2005).

* cited by examiner

ANTIBACTERIAL AGENTS: ARYLALKYLCARBOXAMIDO PHLOROGLUCINOLS

CROSS-REFERENCE TO RELATED APPLICATION(S)

This application claims priority to U.S. Provisional Application No. 62/639,352, filed Mar. 6, 2018, which is hereby incorporated by reference in its entirety.

GOVERNMENT FUNDING

This invention was made with government support under grant number AI109713 awarded by the National Institutes of Health. The government has certain rights in the invention.

BACKGROUND

Bacterial infectious diseases kill 100,000 persons each year in the US and 11 million persons each year worldwide, representing nearly a fifth of deaths each year worldwide (Heron et al., Final Data for 2006. National Vital Statistics Reports, Vol. 57 (Centers for Disease Control and Prevention, Atlanta Ga.) and World Health Organization (2008) The Global Burden of Disease: 2004 Update (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports,* 122, 160-166; Scott, R. (2009) *The direct medical costs of healthcare-associated infections in U.S. hospitals and benefits of prevention* (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a proven target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* 14, 532-543). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are highly conserved in human RNAP I, RNAP II, and RNAP III (permitting therapeutic selectivity).

The rifamycin antibacterial agents function by binding to and inhibiting bacterial RNAP (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). The rifamycins bind to a site on bacterial RNAP adjacent to the RNAP active center and prevent extension of RNA chains beyond a length of 2-3 nt. The rifamycins are in current clinical use in treatment of both Gram-positive and Gram-negative bacterial infections. The rifamycins are of particular importance in treatment of tuberculosis; the rifamycins are first-line anti-tuberculosis agents and are among the few antituberculosis agents able to kill non-replicating tuberculosis bacteria.

The clinical utility of the rifamycin antibacterial agents is threatened by the existence of bacterial strains resistant to rifamycins (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). Resistance to rifamycins typically involves substitution of residues in or immediately adjacent to the rifamycin binding site on bacterial RNAP—i.e., substitutions that directly decrease binding of rifamycins.

In view of the public-health threat posed by rifamycin-resistant and multidrug-resistant bacterial infections, there is an urgent need for new antibacterial agents that (i) inhibit bacterial RNAP (and thus have the same biochemical effects as rifamycins), but that (ii) inhibit bacterial RNAP through binding sites that do not overlap the rifamycin binding site (and thus do not share cross-resistance with rifamycins).

SUMMARY

The invention provide compounds—arylalkylcarboxamido (ACTs)—that inhibit bacterial RNA polymerase and inhibit bacterial growth.

Accordingly, in one embodiment the invention provides a compound of formula I or II:

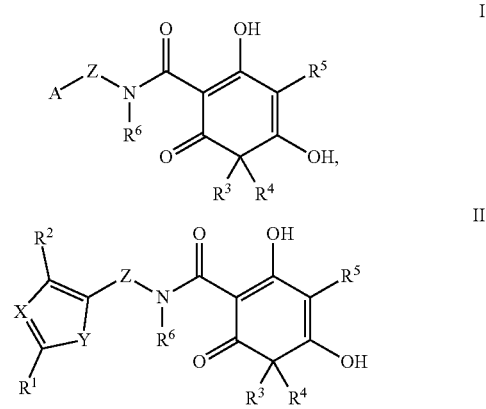

or a tautomer or a salt thereof, wherein:

X and Y are individually carbon, sulfur, oxygen, or nitrogen, wherein at least one of X and Y is other than carbon;

Z is a linker comprising —C(R$^a$R$^b$)—, —C(R$^a$R$^b$)C(R$^c$R$^d$)—, or —C(R$^a$R$^b$)C(R$^c$R$^d$)C(R$^e$R$^f$)—;

A is a phenyl ring that is optionally substituted with one or more groups independently selected from the group consisting of halo, (C$_1$-C$_6$)alkyl, (C$_2$-C$_6$)alkenyl, (C$_1$-C$_6$)alkoxy, aryl-(C$_1$-C$_6$)alkyl-, aryloxy, and heteroaryloxy, wherein any (C$_1$-C$_6$)alkyl, (C$_2$-C$_6$)alkenyl, and (C$_1$-C$_6$)alkoxy is optionally is substituted by one or more halo, and wherein any aryl-(C$_1$-C$_6$)alkyl-, aryloxy, and heteroaryloxy is optionally substituted by one or more groups independently selected from the group consisting of halo, (C$_1$-C$_6$)alkyl, (C$_2$-C$_6$)alkenyl, (C$_1$-C$_6$)alkoxy, aryl, heteroaryl, morpholino, piperazinyl, and —CONR$^w$R$^x$, which (C$_1$-C$_6$)alkyl, (C$_2$-C$_6$)alkenyl, (C$_1$-C$_6$)alkoxy, aryl, heteroaryl, morpholino, or piperazinyl optionally is substituted with halo;

R$^1$ is H, halo, (C$_1$-C$_6$)alkyl, (C$_2$-C$_6$)alkenyl, or (C$_1$-C$_6$)alkoxy, which (C$_1$-C$_6$)alkyl, (C$_2$-C$_6$)alkenyl, or (C$_1$-C$_6$)alkoxy optionally is substituted with halo; or R$^1$ is aryl-(C$_1$-C$_6$)alkyl-, aryloxy, or heteroaryloxy, which aryl-(C$_1$-C$_6$)alkyl-, aryloxy, or heteroaryloxy optionally is substituted by one or more of halo, (C$_1$-C$_6$)alkyl, (C$_2$-C$_6$)alkenyl, or (C$_1$-C$_6$)alkoxy, aryl, heteroaryl, morpholino, piperazinyl, and —CONR$^y$R$^z$, which (C$_1$-C$_6$)alkyl, (C$_2$-C$_6$)alkenyl, (C$_1$-C$_6$)alkoxy, aryl, heteroaryl, morpholino, or piperazinyl optionally is substituted with halo;

R$^2$ is H, halo, (C$_1$-C$_6$)alkyl, (C$_2$-C$_6$)alkenyl, or (C$_1$-C$_6$)alkoxy, which (C$_1$-C$_6$)alkyl, (C$_2$-C$_6$)alkenyl, or (C$_1$-C$_6$)alkoxy optionally is substituted with halo;

R$^3$ is H, halo, (C$_1$-C$_8$)alkyl, or (C$_2$-C$_8$)alkenyl, which (C$_1$-C$_6$)alkyl, or (C$_2$-C$_8$)alkenyl optionally is substituted with one or more of halo, oxo, hydroxy, —CO$_2$R$^t$, —CONR$^u$R$^v$, cyano, —NR$^g$R$^h$R$^i$, sulfonate, fluoromethoxy, difluoromethoxy, trifluoromethoxy, (C$_1$-C$_8$)alkyl, (C$_2$-C$_8$)alkenyl, (C$_1$-C$_8$)alkoxy, aryl, heteroaryl, aryloxy, or heteroaryloxy;

R$^4$ is H, halo, (C$_1$-C$_8$)alkyl, or (C$_2$-C$_8$)alkenyl, which (C$_1$-C$_8$)alkyl, or (C$_2$-C$_8$)alkenyl optionally is substituted with one or more of halo, oxo, hydroxy, —CO$_2$R$^k$, —CONR$^m$R$^n$, cyano, —NR$^g$R$^h$R$^i$, sulfonate, fluoromethoxy, difluoromethoxy, trifluoromethoxy, (C$_1$-C$_8$)alkyl, (C$_2$-C$_8$)alkenyl, (C$_1$-C$_8$)alkoxy, aryl, heteroaryl, aryloxy, or heteroaryloxy;

R$^5$ is H, halo, (C$_1$-C$_8$)alkyl, or (C$_1$-C$_8$)alkenyl, which (C$_1$-C$_8$)alkyl, or (C$_2$-C$_8$)alkenyl optionally is substituted with one or more of halo, oxo, hydroxy, —CO$_2$R$^p$, —CON$^r$R$^s$, cyano, —NR$^g$R$^h$R$^i$, sulfonate, fluoromethoxy, difluoromethoxy, trifluoromethoxy, (C$_1$-C$_8$)alkyl, (C$_2$-C$_8$)alkenyl, (C$_1$-C$_8$)alkoxy, aryl, heteroaryl, aryloxy, or heteroaryloxy;

R$^6$ is H, (C$_1$-C$_6$)alkyl or (C$_2$-C$_6$)alkenyl, which (C$_1$-C$_8$)alkyl or (C$_2$-C$_6$)alkenyl optionally is substituted with halo;

R$^a$, R$^b$, R$^c$, R$^d$, R$^e$, and R$^f$ each independently is absent, H, halo, (C$_1$-C$_6$)alkyl, (C$_2$-C$_6$)alkenyl, or (C$_1$-C$_6$)alkoxy, which (C$_1$-C$_6$)alky (C$_2$-C$_6$)alkenyl, or (C$_1$-C$_6$)alkoxy optionally is substituted with halo; or R$^a$, R$^b$, and the carbon to which they are attached, or R$^c$, R$^d$, and the carbon to which they are attached, or R$^e$, R$^f$, and the carbon to which they are attached, form a cylopropyl ring; or R$^a$ and the carbons to which R$^a$ and R$^c$ are attached, or R$^c$ and the carbons to which R$^c$ and R$^e$ are attached, form a cylopropyl ring;

R$^g$ and R$^h$ each independently is H or (C$_1$-C$_6$)alkyl, or W and R$^h$, together with the nitrogen to which they are attached, form a morpholino, piperazino, pyrrolidino, or piperidino; and each R$^i$ independently is absent, H, or (C$_1$-C$_6$)alkyl, provided that when R$^i$ is H or (C$_1$-C$_6$) alkyl and the nitrogen to which R$^1$ is attached is a positively charged ammonium nitrogen, then the positively charged ammonium nitrogen is associated with a pharmaceutically acceptable counter ion M;

R$^k$ is H or (C$_1$-C$_6$)alkyl;

R$^m$ and R$^n$ each independently is H or (C$_1$-C$_6$)alkyl that is optionally substituted with one or more of halo;

R$^p$ is H or (C$_1$-C$_6$)alkyl that is optionally substituted with one or more of halo;

R$^r$ and R$^s$ each independently is H or (C$_1$-C$_6$)alkyl that is optionally substituted with one or more of halo;

R$^t$ is H or (C$_1$-C$_6$)alky that is optionally substituted with one or more of halo I;

R$^u$ and R$^v$ each independently is H or (C$_1$-C$_6$)alkyl that is optionally substituted with one or more of halo;

R$^w$ and R$^x$ each independently is H or (C$_1$-C$_6$)alkyl that is optionally substituted with one or more of halo; and R$^y$ and R$^z$ each independently is H or (C$_1$-C$_6$)alkyl that is optionally substituted with one or more of halo.

The invention also provides a compound of formula I or II or a tautomer or salt thereof for use in the prophylaxis or treatment of a bacterial infection.

The invention also provides a composition comprising a compound of formula I or II or a tautomer or a pharmaceutically acceptable salt thereof and a pharmaceutically acceptable carrier.

The invention also provides the use of a compound of formula I or II or a tautomer or salt thereof as an inhibitor of a bacterial RNA polymerase.

The invention also provides the use of a compound of formula I or II or a tautomer or salt thereof as an antibacterial agent.

The invention also provides the use of a compound of formula I or II or a tautomer or salt thereof as a disinfectant, a sterilant, an antispoilant, an antiseptic, or an antiinfective.

The invention also provides the use of a compound of formula I or II or a tautomer or a pharmaceutically acceptable salt thereof for the preparation of a medicament for prophylaxis or treatment of a bacterial infection in a mammal.

The invention also provides a method of inhibiting a bacterial RNA polymerase, comprising contacting a bacterial RNA polymerase with a compound of formula I or II or a tautomer or salt thereof.

The invention also provides a method of treating a bacterial infection in a mammal, comprising administering to the mammal a therapeutically effective amount of a compound of formula I or II or a tautomer or a pharmaceutically acceptable salt thereof.

The invention provides new compositions of matter—arylalkylcarboxamido (ACTs)—that inhibit bacterial RNA polymerase and inhibit bacterial growth.

Compounds of this invention differ from the arylpropanoyl phloroglucinols, arylpropenoyl phloroglucinols, and arylcyclopropanoyl phloroglucinols of U.S. Pat. No. 9,517,994, PCT/US11/50708, and PCT/US16/65931, by having a carboxamido-containing, rather than a keto-containing, linker between the aryl or heteroaryl moiety and the phloroglucinol-derived moiety.

Certain representative compounds of this invention exhibited higher RNA-polymerase-inhibitory activities, higher in vitro antibacterial activities, higher in vivo antibacterial activities, or lower toxicities, as compared to the previous arylpropanoyl phloroglucinols, arylpropenoyl phloroglucinols, and arylcyclopropanoyl phloroglucinols of U.S. Pat. No. 9,517,994, PCT/US11/50708, and PCT/US16/65931.

Certain representative compounds of this invention exhibited potent in vitro RNA-polymerase-inhibitory activities (micromolar or better $IC_{50s}$), potent in vitro antibacterial activities (micromolar or better MICs, and potent in vivo antibacterial activities in a mouse methicillin-resistant *Staphylococcus aureus* (MRSA) peritonitis model (≤10 mg/kg ED50s).

Compounds of this invention have applications in analysis of RNA polymerase structure and function, control of bacterial gene expression, control of bacterial growth, antibacterial chemistry, antibacterial therapy, or drug discovery.

DETAILED DESCRIPTION

The following definitions are used, unless otherwise indicated.

The term "halo" means fluoro, chloro, bromo, or iodo.

The term "alkyl" used alone or as part of a larger moiety, includes both straight and branched chains. For example, $C_1$-$C_8$ alkyl includes both straight and branched chained alkyl groups having from one to eight carbon atoms. The term alkyl also includes cycloalkyl groups (e.g. cyclopropyl, cyclobutyl, cyclopentyl, cyclohexyl, cycloheptyl, and cyclooctyl), as well as (cycloalkyl)alkyl groups (e.g. 3-cyclohexylpropyl, cyclopentylmethyl, 2-cyclohexylethyl, and 2-cyclopropylethyl).

The term "alkenyl" used alone or as part of a larger moiety, includes an alkyl that has one or more double bonds. For example, $C_2$-$C_8$ alkenyl includes both straight and branched chained groups having from two to eight carbon atoms and one or more (e.g. 1, 2, or 3) double bonds, as well as cycloalkyl and (cycloalkyl)alkyl groups having one or more double bonds in the cycloalkyl portion or in the alkyl portion of the (cycloalkyl)alkyl.

The term "alkoxy" used alone or as part of a larger moiety is a group alkyl-O—, wherein alkyl has any of the values defined herein.

The term "aryl" denotes a phenyl radical or an ortho-fused bicyclic carbocyclic radical having about nine to ten ring atoms in which at least one ring is aromatic. For example, aryl can be phenyl, indenyl, or naphthyl.

The term "heteroaryl" encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$) alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X). For example heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "aryloxy" means (aryl)-O—.

The term "heteroaryloxy" means (heteroaryl)-O—.

The term "sulfonate" means $SO_3H$.

A combination of substituents or variables is permissible only if such a combination results in a stable or chemically feasible compound. The term "salts," as used herein, refers to salts which possess stability sufficient to allow for their manufacture and which maintain the integrity of the salt for a sufficient period of time to be useful for the purposes detailed herein (e.g., formulation into therapeutic products, intermediates for use in production of pharmaceutically acceptable salts, isolatable or storable intermediate salts, treating a disease or condition responsive to therapeutic agents.

Unless otherwise stated, structures depicted herein are also meant to include all stereochemical forms of the structure (i.e., the R and S configurations for each asymmetric center). Therefore, single stereochemical isomers, as well as enantiomeric and diastereomeric mixtures, of the present compounds are within the scope of the invention. Similarly, E- and Z-isomers, or mixtures thereof, of olefins within the structures also are within the scope of the invention.

Unless otherwise stated, structures depicted herein also are meant to include compounds that include one or more isotopically enriched atoms. For example, compounds having the present structures except for the replacement of a hydrogen atom by a deuterium or tritium, or the replacement of a carbon by a $^{13}$C- or $^{14}$C-enriched carbon, are within the scope of this invention.

Compounds of this invention may exist in tautomeric forms, such as keto-enol tautomers. The depiction of a single tautomer is understood to represent the compound in all of its tautomeric forms. For example, a compound of formula I, wherein $R^3$ is hydrogen, can be exist as, and be depicted herein, as either of the following two tautomeric forms:

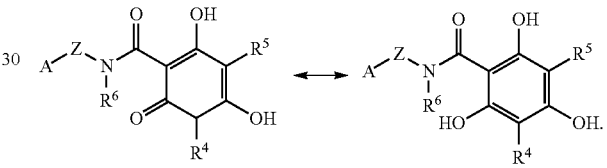

The term "pharmaceutically acceptable," as used herein, refers to a salt that is, within the scope of sound medical judgment, suitable for use in contact with the tissues of humans and other mammals without undue toxicity, irritation, allergic response and the like, and are commensurate with a reasonable benefit/risk ratio. In one embodiment, a salt is a pharmaceutically acceptable salt.

Embodiments

In one embodiment, the invention provides a compound of formula I, or a tautomer or a salt thereof.

In one embodiment, A is a phenyl ring that is optionally substituted with one or more groups independently selected from the group consisting of halo, ($C_1$-$C_6$)alkyl that is optionally is substituted by one or more halo, aryl-($C_1$-$C_6$) alkyl-, aryloxy, and heteroaryloxy, wherein any aryl-($C_1$-$C_6$) alkyl-, aryloxy, and heteroaryloxy is optionally substituted by one or more groups $R^{aa}$, which $R^{aa}$ independently is selected from the group consisting of halo, ($C_1$-$C_6$)alkyl, ($C_1$-$C_6$)alkoxy, heteroaryl, morpholino, piperazinyl, and —$CONR^wR^x$, wherein any ($C_1$-$C_6$)alkyl, (($C_1$-$C_6$)alkoxy, heteroaryl, morpholino, or piperazinyl of $R^{aa}$ optionally is substituted with halo.

In one embodiment, A is a phenyl ring that is optionally substituted with one or more groups independently selected from the group consisting of halo and ($C_1$-$C_6$)alkyl that is optionally is substituted by one or more halo.

In one embodiment, A is a phenyl ring that is optionally substituted with one or more groups independently selected from the group consisting of aryl-($C_1$-$C_6$)alkyl-, aryloxy, and heteroaryloxy, wherein any aryl-($C_1$-$C_6$)alkyl-, aryloxy, and heteroaryloxy is optionally substituted by one or more groups independently selected from the group consisting of halo, $(C_1-C_6)$alkyl, $(C_1-C_6)$alkoxy, heteroaryl, morpholino, piperazinyl, and $CONR^wR^x$, which $(C_1-C_6)$alkyl, $((C_1-C_6)$alkoxy, heteroaryl, morpholino, or piperazinyl optionally is substituted with halo.

In one embodiment, each aryl is phenyl and wherein each heteroaryl is a 6-membered heteroaryl ring comprising 1 or 2 nitrogens.

In one embodiment, A is selected from the group consisting of:

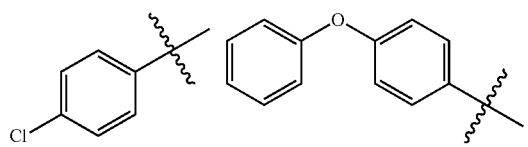
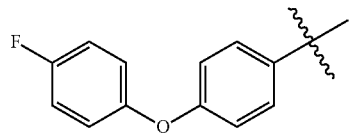
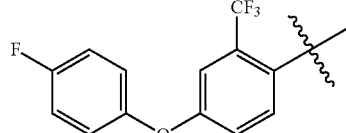
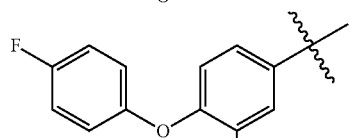
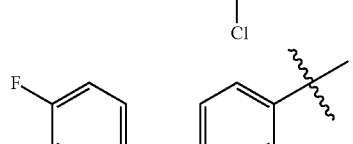
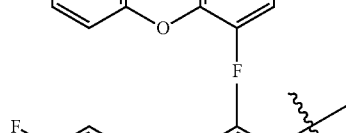
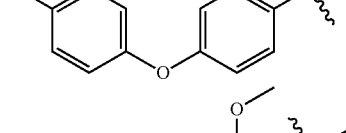
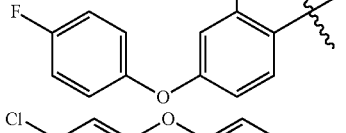
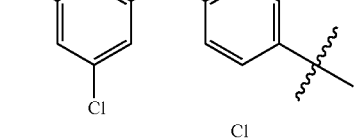
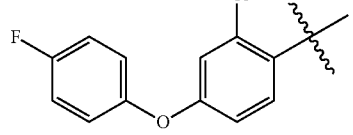

-continued

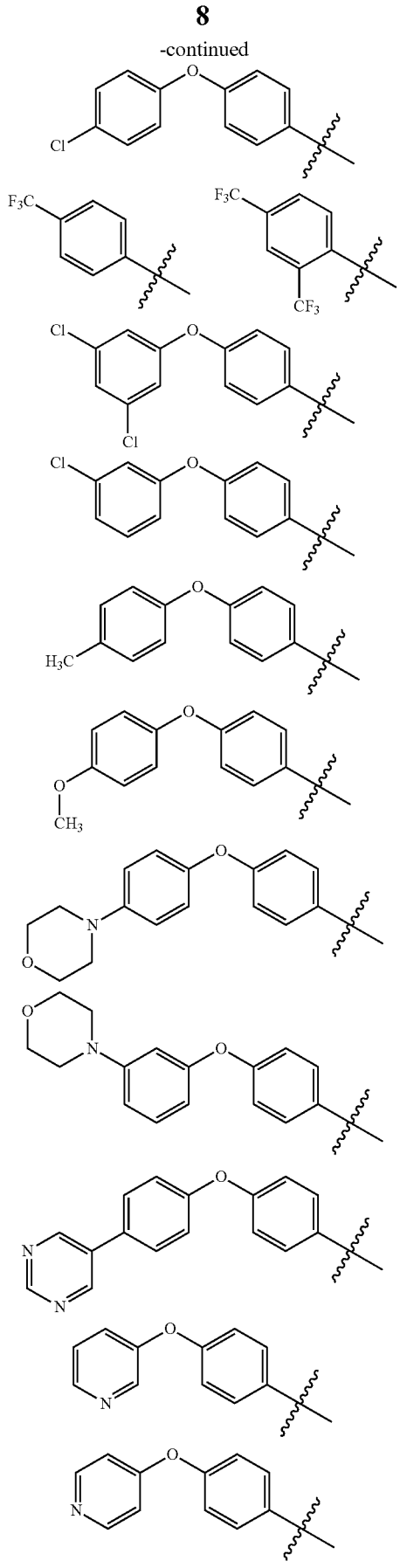

-continued

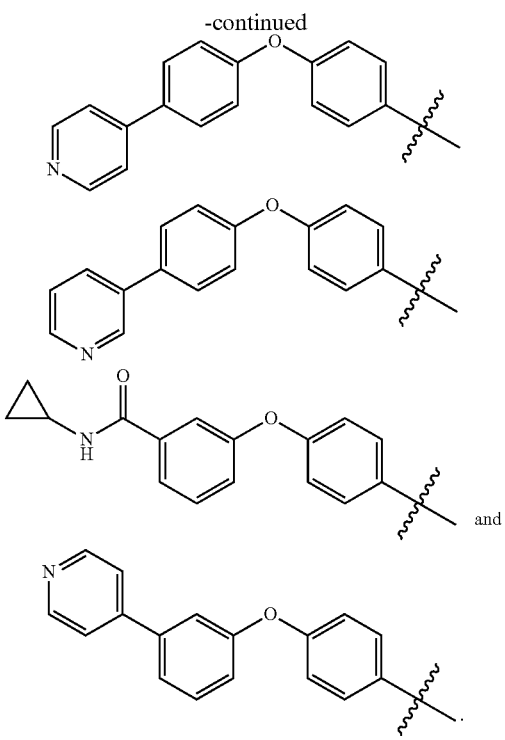

In one embodiment, the invention provides a compound of formula II, or a tautomer or a salt thereof.

In one embodiment, the invention provides a compound of Ia:

Ia or a tautomer or a salt thereof, wherein:

$R^1$ is H, halo, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo; or $R^1$ is aryl-$(C_1-C_6)$alkyl-, aryloxy, or heteroaryloxy, which aryl-$(C_1-C_6)$alkyl-, aryloxy, or heteroarlyoxy optionally is substituted by one or more of halo, $(C_1-C_6)$alkyl, $(C_2-C_6)$alkenyl, $(C_1-C_6)$alkoxy, aryl, heteroaryl, morpholino, piperazinyl, and —CONR$^y$R$^z$, which $(C_1-C_6)$alkyl, $(C_2-C_6)$alkenyl, $(C_1-C_6)$alkoxy, aryl, heteroaryl, morpholino, and piperazinyl is optionally is substituted with halo; and $R^2$ is H, halo, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo.

Antibacterial Agents

The invention provides new compositions of matter that highly potently inhibit bacterial RNA polymerase and inhibit bacterial growth. Certain embodiments of the invention also provide methods for preparation of a compound of formula I or II.

Certain embodiments of the invention also provide an assay for inhibition of a RNA polymerase comprising contacting a bacterial RNA polymerase with a compound of formula I or II or a tautomer or salt thereof.

Certain embodiments of the invention also provide an assay for antibacterial activity comprising contacting a bacterial RNA polymerase with a compound of formula I or II or a tautomer or salt thereof.

Certain embodiments of the invention also provide the use of a compound of formula I or II or a tautomer or salt thereof as an inhibitor of a bacterial RNA polymerase.

Certain embodiments of the invention also provide the use of a compound of formula I or II or a tautomer or salt thereof as an antibacterial agent.

Certain embodiments of the invention also provide the use of a compound of formula I or II or a tautomer or salt thereof as one of a disinfectant, a sterilant, an antispoilant, an antiseptic, or an antiinfective.

Administration of Pharmaceutical Compositions

A compound of formula I or II or a tautomer or a pharmaceutically acceptable salt thereof may be formulated as pharmaceutical compositions and administered to a mammalian host, such as a human patient in a variety of forms adapted to the chosen route of administration (i.e., orally or parenterally, by intravenous, intramuscular, topical or subcutaneous routes).

Thus, the compound of formula I or II or a tautomer or a pharmaceutically acceptable salt thereof may be systemically administered, e.g., orally, in combination with a pharmaceutically acceptable vehicle such as an inert diluent or an assimilable edible carrier. The compound of formula I or II or a tautomer or a pharmaceutically acceptable salt thereof may be enclosed in hard or soft shell gelatin capsules, may be compressed into tablets, or may be incorporated directly with the food of the patient's diet. For oral therapeutic administration, the compound of formula I or II or a tautomer or a pharmaceutically acceptable salt thereof may be combined with one or more excipients and used in the form of ingestible tablets, buccal tablets, troches, capsules, elixirs, suspensions, syrups, wafers, and the like. Such compositions and preparations should contain at least 0.1% of the compound of formula I or II or a tautomer or a pharmaceutically acceptable salt thereof. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound of formula I or II or a tautomer or a pharmaceutically acceptable salt thereof may be incorporated into sustained-release preparations and devices.

The compound of formula I or II or a tautomer or a pharmaceutically acceptable salt thereof may also be administered intravenously or intraperitoneally by infusion or injection. Solutions of the active compound or its pharmaceutically acceptable salt can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound of formula I or II or a tautomer or a pharmaceutically acceptable salt thereof in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the compound of formula I or II or a tautomer or a pharmaceutically acceptable salt thereof may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compound of formula I or II or a tautomer or a pharmaceutically acceptable salt thereof to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compound of formula I or II or a tautomer or a pharmaceutically acceptable salt thereof can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound of formula I or II or a tautomer or a pharmaceutically acceptable salt thereof required for use in treatment will vary not only with the particular compound or salt selected but also with the route of administration, the nature of the condition being treated and the age and condition of the patient and will be ultimately at the discretion of the attendant physician or clinician.

The compound of formula I or II or a tautomer or a pharmaceutically acceptable salt thereof is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of formula I or II formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Preparation

Compounds of this invention can be synthesized, by way of example, as illustrated in Schemes 1-3.

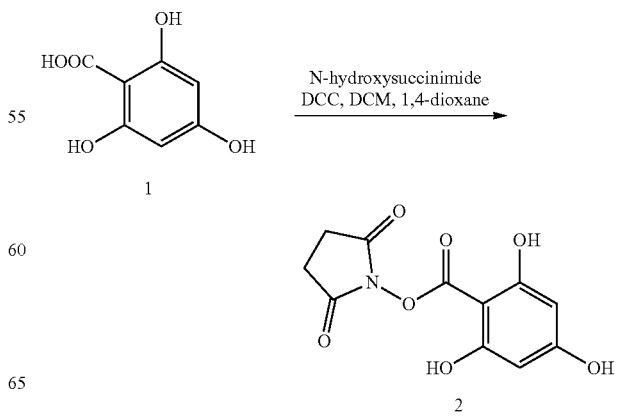

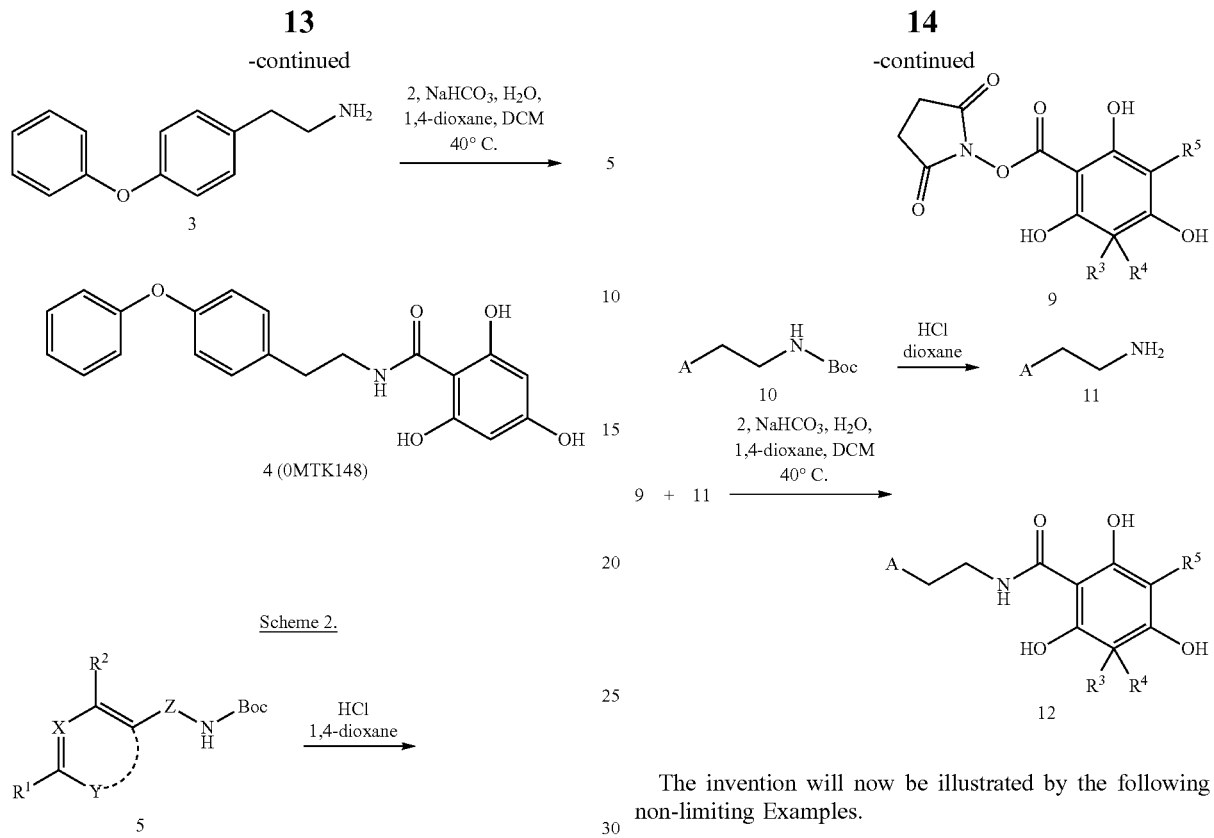

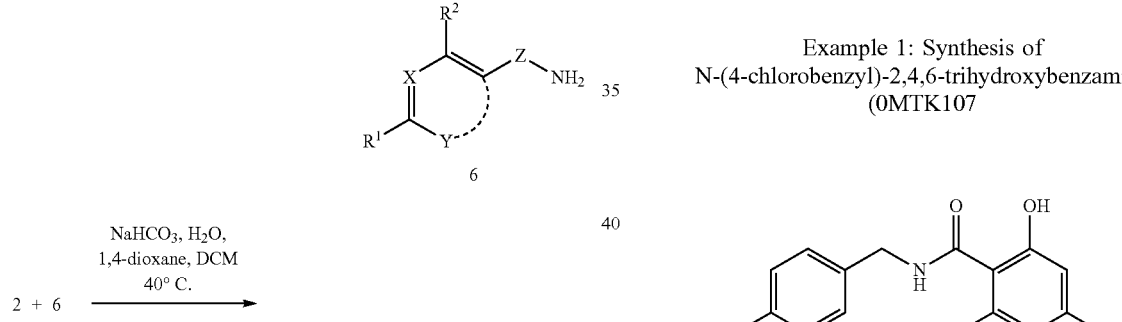

Scheme 2.

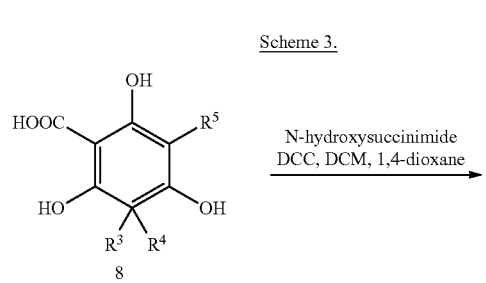

Scheme 3.

The invention will now be illustrated by the following non-limiting Examples.

EXAMPLES

Example 1: Synthesis of N-(4-chlorobenzyl)-2,4,6-trihydroxybenzamide (0MTK107

To 2,4,6-trihydroxybenzoic acid monohydrate (188 mg; 1.00 mmol) in 1,4-dioxane (2.0 ml), was added 1.0 M DCC in DCM (1.00 ml; 1.00 mmol) and N-hydroxy succinimide (115 mg, 1.00 mmol), and the reaction mixture was stirred at room temperature under nitrogen overnight. The reaction mixture was filtered, the residue was washed with 1,4-dioxane (1.00 ml), and the filtrate and wash were pooled to afford a solution of 2,5-dioxopyrrolidin-1-yl 2,4,6-trihydroxybenzoate.

To the resulting solution of 2,5-dioxopyrrolidin-1-yl 2,4,6-trihydroxybenzoate (3.00 ml; ~1.00 mmol), was added 4-chlorobenzylamine (247 mg; 1.00 mmol), 1,4-dioxane (1.00 ml), and 10% $NaHCO_3$ (1.00 ml), and the reaction mixture was heated 2 h at 40° C., and then cooled to room temperature. The reaction mixture was supplemented with 10% aqueous citric acid (10 ml) and was extracted with ethyl acetate (2×40 ml), and the pooled organic extracts were washed with saturated aqueous brine solution (20 ml), dried over anhydrous $Na_2SO_4$, filtered, and evaporated under vacuum. The crude material was subjected to flash column chromatography on silica gel, eluting with 0-30% ethyl acetate in hexane, to afford N-(4-chlorobenzyl)-2,4,6-trihydroxybenzamide (0MTK107) as a white solid (185 mg, 0.629 mmol, 63% yield).

MS: m/z 297.0, [M+H]$^+$; $^1$H NMR (500 MHz, d$_6$-DMSO) δ 12.52 (s, 2H), 9.93 (s, 1H), 9.06 (t, J=5.5 Hz, 1H), 7.39 (d, J=8.5 Hz, 2H), 7.33 (d, J=8.5 Hz, 2H), 5.81 (s, 2H), 4.49 (d, J=6.0 Hz, 2H); also noted, 3.32 (s) water.

Example 2: Synthesis of N-(4-chlorophenethyl)-2,4,6-trihydroxybenzamide (0MTK127

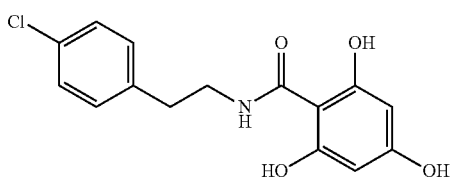 [SMILES: O=C(NCCc1ccc(Cl)cc1)c1c(O)cc(O)cc1O]

0MTK127 was synthesized as described for 0MTK107, but replacing 4-chlorobenzylamine with (4-chlorophenyl)ethan-1-amine.

White solid. MS: m/z 308.0, [M+H]$^+$; $^1$H NMR (500 MHz, d$_6$-DMSO) δ 12.5 (br s, 2), 9.88 (s, 1), 8.61 (br s, 1), 7.36 (d, J=7.5 Hz, 2), 7.29 (d, J=8.0 Hz, 2), 5.77 (s, 2), 3.54 (q, J=6.5 Hz, 2), 2.83 (t, J=7.0 Hz, 2); also noted, 3.32 (s, H$_2$O).

Example 3: Synthesis of N-(4-chlorophenethyl)-2,4,6-trihydroxy-N-methylbenzamide (0MTK128

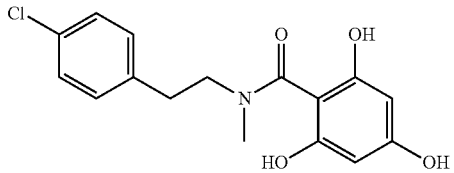 [SMILES: CN(CCc1ccc(Cl)cc1)C(=O)c1c(O)cc(O)cc1O]

0MTK128 was synthesized as described 0MTK107, but replacing 4-chlorobenzylamine with N-[2-(4-chlorophenyl)ethyl]-N-methylamine.

White solid. MS: m/z 322.0, [M+H]$^+$; $^1$H NMR (500 MHz, d$_6$-DMSO) δ $^1$H NMR (500 MHz, d$_6$-acetone) δ 8.86 (br s, 1), 8.50 (s, 1), 7.29 (d, J=8.5 Hz, 2), 7.25 (t, J=8.5 Hz, 2), 5.96 (s, 2), 3.66 (t, J=7.0 Hz, 2), 2.99 (s, 3), 2.93 (t, J=7.5 Hz, 2); also noted, 2.81 (s, H$_2$O), 2.78 (s).

Example 4: Synthesis of N-(2-(4-chlorophenyl)-2-methylpropyl)-2,4,6-trihydroxybenzamide (0MTK146

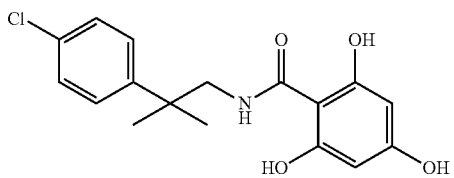 [SMILES: CC(C)(CNC(=O)c1c(O)cc(O)cc1O)c1ccc(Cl)cc1]

0MTK146 was synthesized as described for 0MTK107, but replacing 4-chlorobenzylamine with 2-(4-chlorophenyl)-2-methylpropan-1-amine.

White solid. MS: m/z 366.0, [M+H]r; $^1$H NMR (500 MHz, d$_6$-DMSO) δ 12.5 (br s, 2), 9.87 (s, 1), 8.39 (t, J=5.5 Hz, 1), 7.45 (d, J=8.0 Hz, 2), 7.39 (d, J=8.0 Hz, 2), 5.74 (s, 2), 3.55 (d, J=5.5 Hz, 2), 1.29 (s, 6); also noted, 4.2 (br s).

Example 5: Synthesis of 2,4,6-trihydroxy-N-(4-phenoxyphenethyl)benzamide (0MTK148

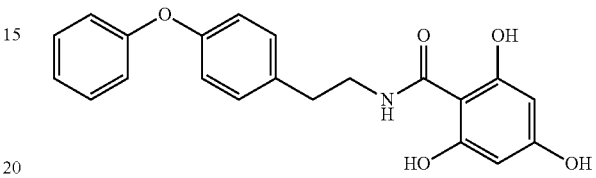

0MTK148 was synthesized as described for 0MTK107, but replacing 4-chlorobenzylamine with 2-(4-phenoxyphenyl)ethanamine.

White solid. MS: m/z 366.0, [M+H]$^+$; $^1$H NMR (500 MHz, d$_6$-DMSO) δ 12.6 (br s, 2), 9.88 (s, 1), 8.64 (s, 1), 7.38 (t, J=7.5 Hz, 2), 7.27 (d, J=7.5 Hz, 2), 7.12 (t, J=7.5 Hz, 1), 6.99-6.94 (m, 4), 5.78 (s, 2), 3.54 (q, J=6.0 Hz, 2), 2.82 (t, J=7.0 Hz, 2); also noted, 3.82 (br s).

Example 6: Synthesis of 2,4,6-trihydroxy-N-(4-phenoxybenzyl)benzamide (0MTK149

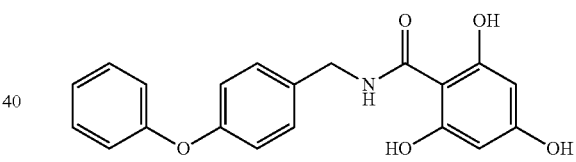

0MTK149 was synthesized as described for 0MTK107, but replacing 4-chlorobenzylamine with 4-phenyloxybenzyl amine.

White solid. MS: m/z 352.0, [M+H]$^+$; $^1$H NMR (500 MHz, d$_6$-DMSO) δ 12.6 (br s, 2), 9.92 (s, 1), 9.03 (t, J=5.5 Hz, 1), 7.39-7.33 (m, 4), 7.12 (t, J=7.0 Hz, 1), 6.99 (d, J=8.0 Hz, 4), 5.81 (s, 2), 4.50 (d, J=5.5 Hz, 2); also noted, 3.6 (br s).

Example 7: Synthesis of N-(4-(4-fluorophenoxy)benzyl)-2,4,6-trihydroxybenzamide (0MTK154

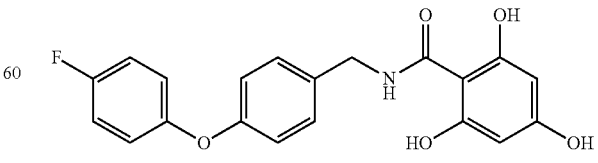

0MTK154 was synthesized as described for 0MTK107, but replacing 4-chlorobenzylamine with 4-(4-fluorophenoxy)benzylamine.

White solid. MS: m/z 370.0, [M+H]+; 1H NMR (500 MHz, d6-DMSO) δ 12.5 (s, 2), 9.92 (s, 1), 9.03 (s, 1), 7.34 (d, J=7.5 Hz, 2), 7.21 (t, J=8.0 Hz, 2), 7.05-7.03 (m, 2), 6.96 (d, J=7.5 Hz, 2), 5.80 (s, 2), 4.49 (d, J=5.0 Hz, 2); also noted, 3.47 (br s).

Example 8: Synthesis of N-(4-(4-fluorophenoxy)-2-(trifluoromethyl)benzyl)-2,4,6-trihydroxybenzamide (OMTK155

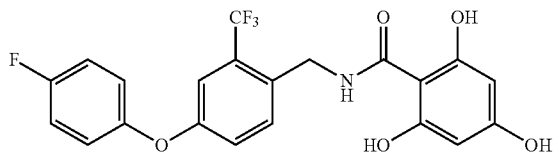

To a solution of 4-fluorophenol (200 mg, 1.78 mmol), 4-bromo-2-(trifluoromethyl)benzonitrile (535 mg; 2.14 mmol), and Cs2CO3 (870 mg; 2.67 mmol) in 1,4-dioxane (10 ml), was added N,N-dimethylglycine hydrochloride (82.0 mg; 0.587 mmol) and copper(I) iodide (34.0 mg; 0.178 mmol), and the reaction mixture was stirred overnight at 100° C. under nitrogen. Saturated sodium chloride in water (10 ml) was added, the mixture was extracted with ethyl acetate (100 ml), and the organic phase was dried over anhydrous Na2SO4, filtered, and evaporated under vacuum. The crude material was subjected to flash column chromatography on silica gel, eluting with 0-80% ethyl acetate in hexane, to afford 4-(4-fluorophenoxy)-2-(trifluoromethyl) benzonitrile as a white solid (173 mg; 0.610 mmol, 34% yield).

To a solution of 4-(4-fluorophenoxy)-2-(trifluoromethyl) benzonitrile (173 mg; 0.610 mmol) in dry THF (3.0 ml), was added 70% Red-Al (0.800 ml, 1.70 mmol) dropwise at 0° C. under nitrogen and the reaction mixture was stirred 3 h at room temperature. Methanol (1.00 ml) and water (1.00 ml) were added, and the mixture was filtered through celite, washed with THF, and concentrated to afford crude 4-(4-fluorophenoxy)-2-(trifluoromethyl)aniline, which was used in the next step without further purification.

To a solution of 2,5-dioxopyrrolidin-1-yl 2,4,6-trihydroxybenzoate in 1,4-dioxane (2.03 ml; ~0.610 mmol), was added crude 4-(4-fluorophenoxy)-2-(trifluoromethyl)aniline (~0.610 mmol), 1,4-dioxane (1.20 ml), and 10% NaHCO3 (1.20 ml), and the reaction mixture was heated 2 h at 40° C. and then cooled to room temperature. The reaction mixture was supplemented with 10% aqueous citric acid (20 ml) and was extracted with ethyl acetate (2×40 ml). and the pooled organic extracts were washed with saturated aqueous brine (20 ml), dried over anhydrous Na2SO4, filtered, and evaporated under vacuum. The crude material was subjected to flash column chromatography on silica gel, eluting with 0-30% ethyl acetate in hexane, to afford N-(4-(4-fluorophenoxy)-2-(trifluoromethyl)benzyl)-2,4,6-trihydroxybenzamide (OMTK155) as a white solid (129 mg, 0.295 mmol, 48% yield for two steps).

MS: m/z 438.0, [M+H]+; 1H NMR (500 MHz, d6-DMSO) δ 12.5 (s, 2), 9.96 (s, 1), 9.11 (t, J=4.5 Hz, 1), 7.53 (d J=9.0 Hz, 1), 7.29-7.25 (m, 4), 7.16-7.13 (m, 2), 5.81 (s, 2), 4.66 (d, J=6.0 Hz, 2); also noted, 3.58 (br s).

Example 9: Synthesis of N-(4-(4-fluorophenoxy) phenethyl)-2,4,6-trihydroxybenzamide (OMTK156

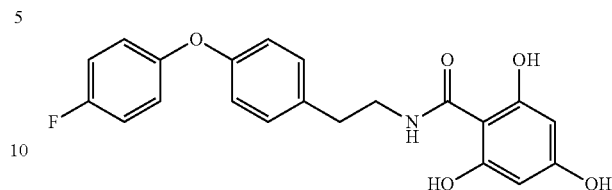

OMTK156 was synthesized as described for OMTK107, but replacing 4-chlorobenzylamine with 2-(4-(4-fluorophenoxy)phenyl)ethanamine.

White solid. MS: m/z 384.0, [M+H]+; 1H NMR (500 MHz, d6-DMSO) δ 12.6 (brs, 2), 9.88 (s, 1), 8.63 (s, 1), 7.27 (d, J=7.0 Hz, 2), 7.21 (t, J=8.0 Hz, 2), 7.04-7.02 (m, 2), 6.93 (d, J=7.0 Hz, 2), 5.78 (s, 2), 3.53 (q, J=7.0 Hz, 2), 2.81 (t, J=6.5 Hz, 2). Also noted 3.8 (br s), 1.7-1.5 (m), 1.2-1.0 (m).

Example 10 Synthesis of 2,4,6-trihydroxy-N-(4-phenoxy-2-(trifluoromethyl)benzyl)benzamide (OMTK158

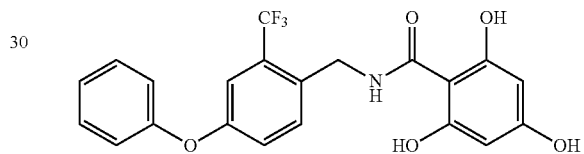

OMTK158 was synthesized as described for OMTK155, but replacing 4-fluorophenol with phenol.

White solid. MS: m/z 420.0, [M+H]+; 1H NMR (500 MHz, d6-DMSO) δ 12.5 (s, 2), 9.98 (s, 1), 9.13 (t, J=6.1 Hz, 1), 7.54 (d, J=8.3 Hz, 1), 7.44 (t, J=8.0 Hz, 2), 7.33-7.27 (m, 2), 7.21 (t, J=7.4 Hz, 1), 7.09 (d, J=7.8 Hz, 2), 5.82 (s, 2), 4.67 (d, J=5.8 Hz, 2). Also noted 3.3 (s, H2O), 1.2 (s).

Example 11 Synthesis of N-(3-chloro-4-(4-fluorophenoxy)benzyl)-2,4,6-trihydroxybenzamide (OMTK174

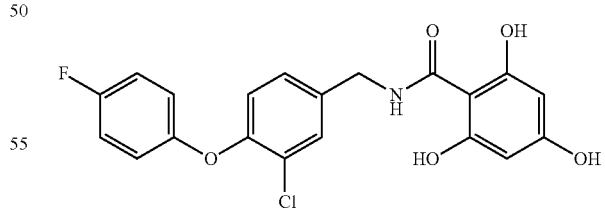

OMTK174 was synthesized as described for OMTK155, but replacing 4-bromo-2-(trifluoromethyl)benzonitrile with 4-bromo-3-chlorobenzonitrile.

White solid. MS: m/z 404.0, [M+H]+; 1H NMR (500 MHz, d6-DMSO) δ 7.50 (s, 1), 7.29 (d, J=8.3 Hz, 1), 7.09 (t, J=7.7 Hz, 2), 7.01-6.97 (m, 1), 6.97-6.91 (m, 2), 5.87 (s, 2), 4.56 (s, 2); also noted, 4.1 (q, EtOAc), 2.0 (s, EtOAc), 1.3 (s), 1.2 (t, EtOAc).

Example 12: Synthesis of N-(3-fluoro-4-(4-fluorophenoxy)benzyl)-2,4,6-trihydroxybenzamide (0MTK175

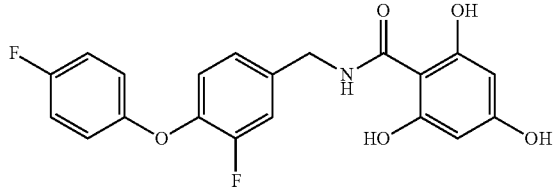

0MTK175 was synthesized as described for 0MTK155, but replacing 4-bromo-2-(trifluoromethyl)benzonitrile with 4-bromo-3-fluorobenzonitrile.

White solid. MS: m/z 388.0, [M+H]$^+$; $^1$H NMR (500 MHz, d$_6$-DMSO) δ 7.24 (d, J=11.6 Hz, 1), 7.16 (d, J=8.3 Hz, 1), 7.11-7.01 (m, 3), 6.96 (d, J=6.8 Hz, 2), 5.87 (s, 2), 4.57 (s, 2), 4.12 (q, J=6.9 Hz, 1); also noted, 7.3 (t), 6.8 (d), 4.1 (q, EtOAc), 2.0 (s, EtOAc), 1.3 (s), 1.2 (t, EtOAc).

Example 13: Synthesis of N-(4-(4-fluorophenoxy)-2-methylbenzyl)-2,4,6-trihydroxybenzamide (0MTK176

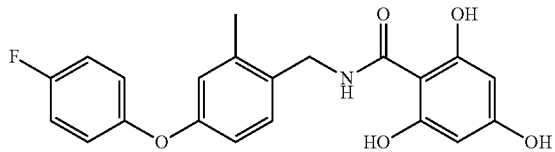 [SMILES: O=C(NCc1ccc(Oc2ccc(F)cc2)cc1)c1c(O)cc(O)cc1O]

0MTK176 was synthesized as described for 0MTK155, but replacing 4-bromo-2-(trifluoromethyl)benzonitrile with 4-bromo-2-methylbenzonitrile.

White solid. MS: m/z 384.0, [M+H]$^+$; $^1$H NMR (500 MHz, d$_6$-DMSO) δ 7.27 (d, J=8.2 Hz, 1), 7.13-7.04 (m, 2), 7.04-6.93 (m, 2), 6.84 (s, 1), 6.77 (d, J=8.0 Hz, 1), 5.86 (s, 2), 4.54 (s, 2), 2.35 (s, 3); also noted, 4.11 (q, EtOAc), 2.03 (s, EtOAc), 1.25 (t, EtOAc).

Example 14: Synthesis of N-(4-(4-fluorophenoxy)-2-methoxybenzyl)-2,4,6-trihydroxybenzamide (0MTK178

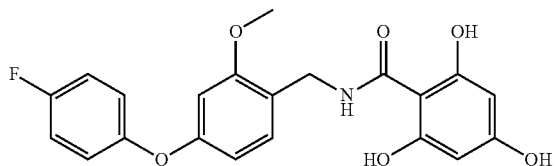 [SMILES: COc1cc(Oc2ccc(F)cc2)ccc1CNC(=O)c1c(O)cc(O)cc1O]

0MTK178 was synthesized as described for 0MTK155, but replacing 4-bromo-2-(trifluoromethyl)benzonitrile with 4-bromo-2-methoxylbenzonitrile.

Colorless oil. MS: m/z 400.0, [M+H]$^+$; $^1$H NMR (500 MHz, d$_6$-DMSO) δ 7.24 (d, J=8.1 Hz, 1), 7.10 (t, J=7.8 Hz, 2), 7.06-6.97 (m, 2), 6.68 (s, 1), 6.48 (d, J=8.1 Hz, 1), 5.85 (s, 2), 4.50 (s, 2), 3.86 (s, 3); also noted, 4.11 (q, EtOAc), 2.03 (s, EtOAc), 1.26 (t, EtOAc).

Example 15: Synthesis of N-(4-(3,5-dichlorophenoxy)phenethyl)-2,4,6-trihydroxybenzamide (0MTK180

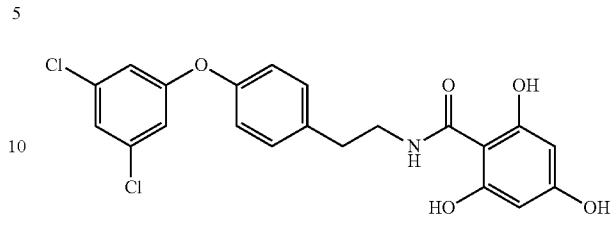

To a solution of (3,5-dichlorophenyl)boronic acid (380 mg; 2.00 mmol) and N-Boc-tyramine (237 mg; 1.00 mmol) in DCM (15.0 ml), was added copper(II) acetate (182 mg; 1.00 mmol), 4 Å molecular sieves (100 mg), and pyridine (0.400 ml, 4.96 mmol), and the reaction mixture was stirred overnight at room temperature with the flask open. The reaction mixture was filtered, the filtrate was concentrated, and the crude material was subjected to flash column chromatography on silica gel, eluting with 0-30% ethyl acetate in hexane, to afford tert-butyl (4-(3,5-dichlorophenoxy)phenethyl)carbamate as a white solid (320 mg; 0.838 mmol; 84% yield).

To the tert-butyl (4-(3,5-dichlorophenoxy)phenethyl)carbamate (320 mg; 0.838 mmol) in DCM (3.00 ml), was added 4.0 N HCl in 1,4-dioxane (1.00 ml; 4.00 mmol), and the reaction mixture was stirred overnight at room temperature. The reaction mixture was concentrated, supplemented with ethyl acetate (100 ml), and washed with Na$_2$CO$_3$ aq. (2×10 ml) and saturated aqueous brine (20 ml), and the organic phase was dried over anhydrous Na$_2$SO$_4$, filtered, and evaporated under vacuum, to afford 2-(4-(3,5-dichlorophenoxy)phenyl)ethan-1-amine as an off-white solid (240 mg; 0.838 mmol, quantitative yield).

To 2,4,6-trihydroxybenzoic acid monohydrate (188 mg; 1.00 mmol) in 1,4-dioxane (2.0 ml), was added 1.0 M DCC in DCM (1.00 ml; 1.00 mmol) and N-hydroxy succinimide (115 mg; 1.00 mmol), and the reaction mixture was stirred overnight at room temperature under nitrogen. The reaction mixture was filtered, the collected residue was washed with 1,4-dioxane (1.00 ml), and the filtrate and wash were pooled, to afford a solution of 2,5-dioxopyrrolidin-1-yl 2,4,6-trihydroxybenzoate.

To the resulting solution of 2,5-dioxopyrrolidin-1-yl 2,4,6-trihydroxybenzoate (3.00 ml; 1.00 mmol), was added 2-(4-(3,5-dichlorophenoxy)phenyl)ethan-1-amine (240 mg; 0.838 mmol), 1,4-dioxane (1.00 ml), and 10% NaHCO$_3$ (1.00 ml), and the reaction mixture was heated 2 h at 40° C. and then cooled to room temperature. The reaction mixture was supplemented with 10% aqueous citric acid (10 ml), was extracted with ethyl acetate (2×40 ml), and the pooled organic extracts were washed with saturated aqueous brine solution (20 ml), dried over anhydrous Na$_2$SO$_4$, filtered, and evaporated under vacuum. The crude material was subjected to flash column chromatography on silica gel, eluting with 0-30% ethyl acetate in hexane, to afford N-(4-(3,5-dichlorophenoxy)phenethyl)-2,4,6-trihydroxybenzamide (0MTK180) as a white solid (150 mg, 0.346 mmol, 41% yield).

MS: m/z 433.8, [M+H]$^+$; $^1$H NMR (500 MHz, d$_6$-DMSO) δ 7.37 (d, J=8.4 Hz, 2), 7.15 (t, J=1.7 Hz, 1), 7.04 (d, J=8.5 Hz, 2), 6.90 (d, J 1.7 Hz, 2), 5.84 (s, 2), 3.65 (t, J=7.0 Hz,

2), 2.94 (t, J=7.0 Hz, 2); also noted, 4.12 (q, EtOAc), 2.03 (s, EtOAc), 1.3 (s), 1.26 (t, EtOAc).

Example 16: Synthesis of N-(2-chloro-4-(4-fluorophenoxy)benzyl)-2,4,6-trihydroxybenzamide (0MTK181

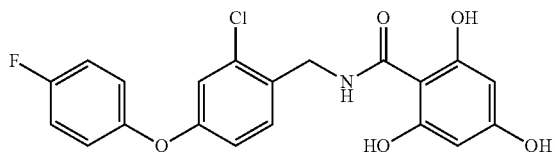 [SMILES: O=C(NCc1ccc(Oc2ccc(F)cc2)cc1Cl)c1c(O)cc(O)cc1O]

0MTK181 was synthesized as described for 0MTK155, but replacing 4-bromo-2-(trifluoromethyl)benzonitrile with 4-bromo-2-chlorobenzonitrile.

Colorless oil. MS: m/z 404.0, [M+H]+; 1H NMR (500 MHz, d6-DMSO) δ 12.5 (s, 2), 9.95 (s, 1), 9.10 (s, 1), 7.37 (d, J=8.6 Hz, 1), 7.26 (dd, J=16.1, 7.5 Hz, 2), 7.15-7.06 (m, 3), 7.00-6.93 (m, 1), 5.82 (s, 2), 4.54 (d, J=5.9 Hz, 2); also noted, 4.03 (q, EtOAc), 3.5 (s, H2O), 2.00 (s, EtOAc), 1.18 (t, EtOAc), 1.92 (s), 1.24 (s), 0.85 (m).

Example 17: Synthesis of N-(4-(4-chlorophenoxy)phenethyl)-2,4,6-trihydroxybenzamide (0MTK183

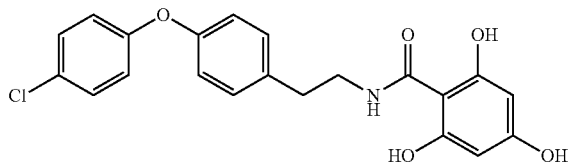 [SMILES: O=C(NCCc1ccc(Oc2ccc(Cl)cc2)cc1)c1c(O)cc(O)cc1O]

0MTK183 was synthesized as described for 0MTK180, but replacing (3,5-dichlorophenyl)boronic acid with (4-chlorophenyl)boronic acid.

White solid. MS: m/z 400.0, [M+H]+; 1H NMR (500 MHz, d6-DMSO) δ 12.6 (br s, 2), 9.87 (s, 1), 8.63 (t, J=6.5 Hz, 1), 7.41 (d, J=9.0 Hz, 2), 7.29 (d, J=8.5 Hz, 2), 7.00-6.97 (m, 4), 5.78 (s, 2), 3.54 (q, J=6.0 Hz, 2), 2.83 (t, J=7.5 Hz, 2); also noted, 11.0 (s), 6.1 (s), 3.54 (br s overlapping quartet, H2O).

Example 18: Synthesis of N-(3-(4-chlorophenyl)propyl)-2,4,6-trihydroxybenzamide (0MTK204

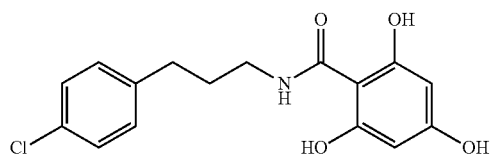 [SMILES: O=C(NCCCc1ccc(Cl)cc1)c1c(O)cc(O)cc1O]

0MTK204 was synthesized as described for 0MTK107, but replacing 4-chlorobenzylamine with 3-(4-chlorophenyl)propan-1-amine.

White solid. MS: m/z 322.0, [M+H]+; 1H NMR (500 MHz, d6-DMSO) δ 12.6 (br s, 2), 9.88 (s, 1), 8.65 (s, 1), 7.33 (d, J=7.0 Hz, 2), 7.25 (d, J=7.5 Hz, 2), 5.79 (s, 2), 3.30-3.27 (m, 2), 2.61 (t, J=7.5 Hz, 2), 1.84-1.78 (m, 2); also noted, 3.46 (br s, H2O).

Example 19: Synthesis of 2,4,6-trihydroxy-N-(4-(trifluoromethyl)phenethyl)benzamide (0MTK207

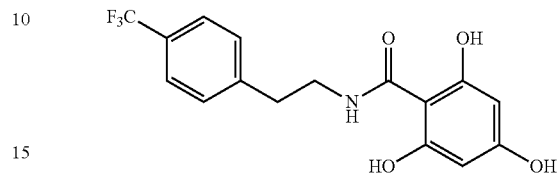

0MTK207 was synthesized as described for 0MTK107, but replacing 4-chlorobenzylamine with 2-(4-(trifluoromethyl)phenyl)ethan-1-amine.

White solid. MS: m/z 342.0, [M+H]+; 1H NMR (500 MHz, d0-DMSO) δ 12.5 (s, 2), 9.89 (s, 1), 8.64 (d, J=5.7 Hz, 1), 7.67 (d, J=8.1 Hz, 2), 7.50 (d, J=8.0 Hz, 2), 5.79 (s, 2), 3.58 (dd, J=13.1, 6.9 Hz, 2), 2.94 (t, J=7.1 Hz, 2); also noted, peaks at 4.03 (q, EtOAc), 3.33 (s, H2O), 1.99 (s, EtOAc), 1.18 (s, EtOAc).

Example 20: Synthesis of N-(2,4-bis(trifluoromethyl)phenethyl)-2,4,6-trihydroxybenzamide (0MTK208

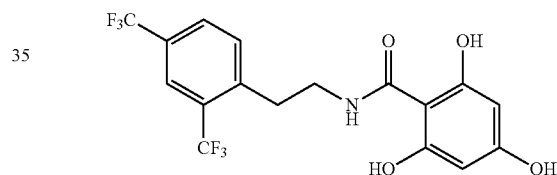

0MTK208 was synthesized as described for 0MTK107, but replacing 4-chlorobenzylamine with 2-(2,4-bis(trifluoromethyl)phenyl)ethan-1-amine.

White solid. MS: m/z 410.0, [M+H]+; 1H NMR (500 MHz, d6-DMSO) δ 12.5 (s, 2), 9.91 (s, 1), 8.73 (t, J=5.7 Hz, 1), 8.05 (d, J=8.8 Hz, 1), 7.99 (s, 1), 7.81 (d, J=8.2 Hz, 1), 5.79 (s, 2), 3.63 (q, J=6.8 Hz, 2), 3.11 (t, J=7.0 Hz, 2). Also noted 4.1 (q, EtOAc), 3.3 (s, H2O), 2.0 (s, EtOAc), 1.3 (s), 1.2 (t, EtOAc).

Example 21: Synthesis of 3,5-dichloro-N-(4-chlorophenethyl)-2,4,6-trihydroxybenzamide (0MTK221

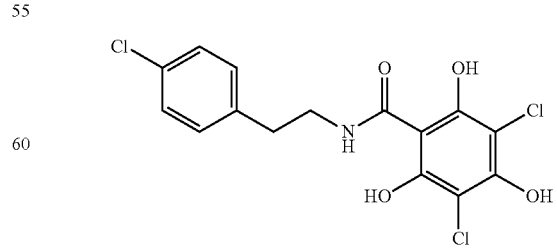

To a solution of N-(4-chlorophenethyl)-2,4,6-trihydroxybenzamide (0MTK127; 30.8 mg; 0.100 mmol) in CHCl3

(1.00 ml), was added 1.0 M sulfuryl chloride solution in DCM (0.200 ml; 0.200 mmol) and EtOH (0.100 ml), the mixture was stirred 1 h at 20° C., and the solvent was evaporated under vacuum. The residue was purified by prep-HPLC (C18, buffer A=0.1% TFA-H$_2$O, buffer B=0.1% TFA-acetonitrile), to afford 3,5-dichloro-N-(4-chlorophenethyl)-2,4,6-trihydroxybenzamide (0MTK221) as a white solid (10.0 mg; 0.0265 mmol; 27% yield).

MS: m/z 375.8, [M+H]$^+$; $^1$H NMR (500 MHz, d$_6$-DMSO) δ 13.1 (br s, 2), 10.7 (s, 1), 8.94 (s, 1), 7.37 (d, J=8.4 Hz, 2), 7.30 (d, J=8.4 Hz, 2), 3.59 (dd, J=12.9, 6.9 Hz, 2), 2.86 (t, J=7.0 Hz, 2). Also noted 4.0 (q, EtOAc), 3.36 (br s, H2O), 2.0 (s, EtOAc), 1.2 (s, EtOAc).

Example 22: Synthesis of 3-chloro-N-(4-chlorophenethyl)-2,4,6-trihydroxybenzamide (0MTK222

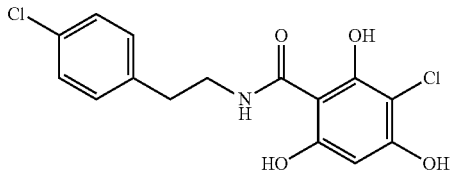 [SMILES: O=C(NCCc1ccc(Cl)cc1)c1c(O)cc(O)c(Cl)c1O]

To a solution of N-(4-chlorophenethyl)-2,4,6-trihydroxybenzamide (0MTK127) (30.8 mg; 0.100 mmol) in CHCl$_3$ (1.00 ml), was added 1.0 M sulfuryl chloride in DCM (0.100 ml; 0.100 mmol) and EtOH (0.100 ml), the reaction mixture was stirred 1 h at 20° C., and the solvent was evaporated under vacuum. The residue was purified by flash column chromatography on silica gel, eluting with 0-30% ethyl acetate in hexane, to afford 3-chloro-N-(4-chlorophenethyl)-2,4,6-trihydroxybenzamide (0MTK222) as a white solid (12.0 mg; 0.0351 mmol; 35% yield).

MS: m/z 341.8, [M+H]% $^1$H NMR (500 MHz, d$_6$-DMSO) δ 14.8 (s, 1), 11.4 (s, 1), 10.6 (s, 1), 8.71 (s, 1), 7.37 (d, J=8.4 Hz, 2), 7.29 (d, J=8.4 Hz, 2), 6.10 (s, 1), 3.56 (dd, J=12.9, 6.9 Hz, 2), 2.85 (t, J=7.1 Hz, 2). Also noted 9.6 (s), 9.2 (s), 5.8 (s), 4.0 (q, EtOAc), 3.3 (s, H2O), 2.0 (s, EtOAc), 1.2 (t, EtOAc).

Example 23: Synthesis of 3-chloro-2,4,6-trihydroxy-N-(4-(trifluoromethyl)phenethyl)benzamide (0MTK223

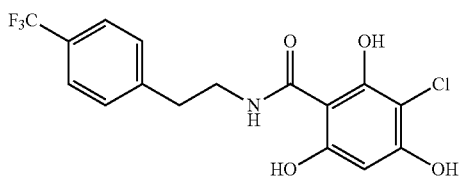 [SMILES: O=C(NCCc1ccc(C(F)(F)F)cc1)c1c(O)cc(O)c(Cl)c1O]

0MTK223 was synthesized as described for 0MTK222, but replacing N-(4-chlorophenethyl)-2,4,6-trihydroxybenzamide with 2,4,6-trihydroxy-N-(4-(trifluoromethyl)phenethyl)benzamide.

White solid. MS: m/z 375.8, [M+H]$^+$; $^1$H NMR (500 MHz, do-DMSO) δ 14.8 (s, 1), 11.4 (s, 1), 10.7 (s, 1), 8.75 (s, 1), 7.68 (d, J=8.1 Hz, 2), 7.50 (d, J=8.0 Hz, 2), 6.11 (s, 1), 3.61 (dd, J=13.1, 6.9 Hz, 2), 2.96 (t, J=7.1 Hz, 2). Also noted 4.0 (q, EtOAc), 3.3 (s, H2O), 2.0 (s, EtOAc), 1.2 (t, EtOAc).

Example 24: Synthesis of 3,5-dichloro-2,4,6-trihydroxy-N-(4-(trifluoromethyl)phenethyl)benzamide (0MTK224

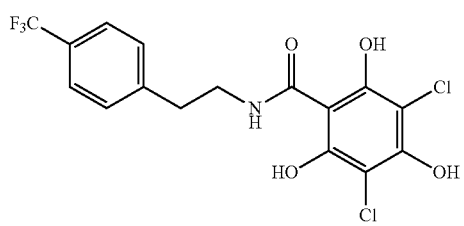 [SMILES: O=C(NCCc1ccc(C(F)(F)F)cc1)c1c(O)c(Cl)c(O)c(Cl)c1O]

0MTK224 was synthesized as described for 0MTK221, but replacing N-(4-chlorophenethyl)-2,4,6-trihydroxybenzamide with 2,4,6-trihydroxy-N-(4-(trifluoromethyl)phenethyl)benzamide.

White solid. MS: m/z 409.8, [M+H]$^+$; $^1$H NMR (500 MHz, do-DMSO) δ 13.1 (br s, 2), 10.6 (s, 1), 9.02 (s, 1), 7.68 (d, J=8.1 Hz, 2), 7.50 (d, J=8.0 Hz, 2), 3.63 (dd, J=12.9, 6.8 Hz, 2), 2.97 (t, J=7.0 Hz, 2); also noted, 5.7 (s), 3.3 (br s, H2O).

Example 25: Synthesis of 3,5-dichloro-2,4,6-trihydroxy-N-(4-phenoxyphenethyl)benzamide (0MTK230

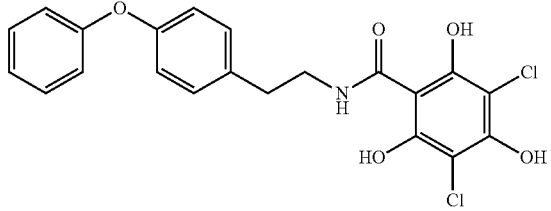 [SMILES: O=C(NCCc1ccc(Oc2ccccc2)cc1)c1c(O)c(Cl)c(O)c(Cl)c1O]

0MTK230 was synthesized as described for 0MTK221, but replacing N-(4-chlorophenethyl)-2,4,6-trihydroxybenzamide with 2,4,6-trihydroxy-N-(4-phenoxyphenethyl)benzamide.

White solid. MS: m/z 434.0, [M+Yi]+; $^1$H NMR (500 MHz, d$_6$-DMSO) δ 13.2 (br s, 2), 10.6 (br s, 1), 9.03 (br s, 1), 7.38 (t, J=7.9 Hz, 2), 7.28 (d, J=8.4 Hz, 2), 7.13 (t, J=7.4 Hz, 1), 6.97 (dd, J=10.9, 8.3 Hz, 4), 3.59 (dd, J=12.7, 6.8 Hz, 2), 2.85 (t, J=7.1 Hz, 2). Also noted peaks at 4.0 (q, EtOAc), 2.0 (s, EtOAc), 1.2 (s), 1.1 (t, EtOAc).

Example 26: Synthesis of 3,5-dichloro-N-(4-(4-fluorophenoxy)phenethyl)-2,4,6-trihydroxybenzamide (0MTK231

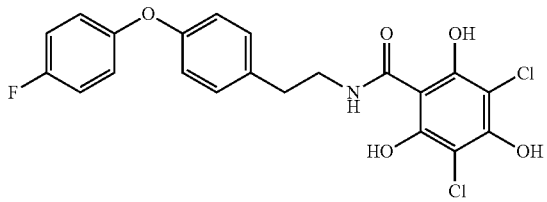 [SMILES: O=C(NCCc1ccc(Oc2ccc(F)cc2)cc1)c1c(O)c(Cl)c(O)c(Cl)c1O]

0MTK231 was synthesized as described for 0MTK221, but replacing N-(4-chlorophenethyl)-2,4,6-trihydroxybenzamide with N-(4-(4-fluorophenoxy)phenethyl)-2,4,6-trihydroxybenzamide.

White solid. MS: m/z 451.8, [M+H]$^+$; $^1$H NMR (500 MHz, d$_6$-DMSO) δ 13.1 (br s, 2), 10.6 (s, 1), 9.02 (br s, 1), 7.28 (d, J=8.6 Hz, 2), 7.25-7.18 (m, 2), 7.07-7.00 (m, 2), 6.94 (d, J=8.5 Hz, 2), 3.58 (dd, J=12.9, 6.8 Hz, 2), 2.84 (t, J=7.1 Hz, 2); also noted, 3.3 (s, H$_2$O), 1.12 (s).

Example 27: Synthesis of 3-chloro-N-(4-(4-chlorophenoxy)phenethyl)-2,4,6-trihydroxybenzamide (0MTK232

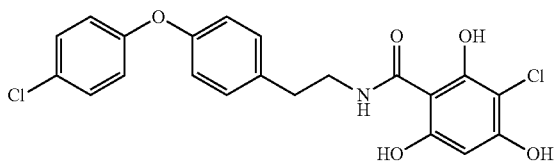 [SMILES: O=C(NCCc1ccc(Oc2ccc(Cl)cc2)cc1)c1c(O)cc(O)c(Cl)c1O]

0MTK232 was synthesized as described for 0MTK222, but replacing N-(4-chlorophenethyl)-2,4,6-trihydroxybenzamide with N-(4-(4-chlorophenoxy)phenethyl)-2,4,6-trihydroxybenzamide.

White solid. MS: m/z 433.8, [M+H]$^+$; $^1$H NMR (500 MHz, do-DMSO) δ 14.8 (s, 1), 11.4 (s, 1), 10.7 (s, 1), 8.74 (t, J=5.5 Hz, 1), 7.42 (d, J=8.9 Hz, 2), 7.30 (d, J=8.5 Hz, 2), 6.99 (dd, J=8.8, 2.8 Hz, 4), 6.11 (s, 1), 3.57 (dd, J=13.0, 6.7 Hz, 2), 2.85 (t, J=7.1 Hz, 2). Also noted peaks at 4.04 (q, EtOAc), 2.00 (s, EtOAc), 1.24 (s), 1.18 (t, EtOAc), 0.85 (m).

Example 28: Synthesis of 3,5-dichloro-N-(4-(4-chlorophenoxy)phenethyl)-2,4,6-trihydroxybenzamide (0MTK233

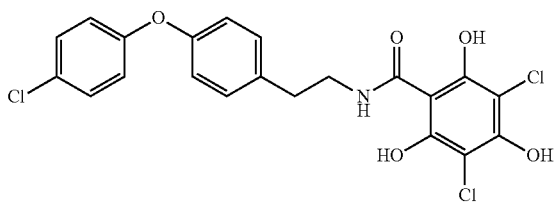 [SMILES: O=C(NCCc1ccc(Oc2ccc(Cl)cc2)cc1)c1c(O)c(Cl)c(O)c(Cl)c1O]

0MTK233 was synthesized as described for 0MTK221, but replacing N-(4-chlorophenethyl)-2,4,6-trihydroxybenzamide with N-(4-(4-chlorophenoxy)phenethyl)-2,4,6-trihydroxybenzamide.

White solid. MS: m/z 467.8, [M+1-1]+; NMR (500 MHz, d$_6$-DMSO) δ 13.2 (br s, 2), 10.6 (s, 1), 9.03 (br s, 1), 7.42 (d, J=8.6 Hz, 2), 7.30 (d, J=7.9 Hz, 2), 6.99 (d, J=6.8 Hz, 4), 3.62-3.56 (m, 2), 2.86 (t, J=7.0 Hz, 2); also noted, 3.3 (s, H$_2$O).

Example 29: Synthesis of 3-chloro-N-(4-(3,5-dichlorophenoxy)phenethyl)-2,4,6-trihydroxybenzamide (0MTK237

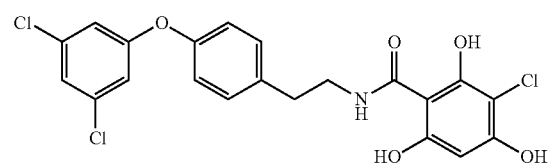 [SMILES: O=C(NCCc1ccc(Oc2cc(Cl)cc(Cl)c2)cc1)c1c(O)cc(O)c(Cl)c1O]

0MTK237 was synthesized as described for 0MTK222, but replacing N-(4-chlorophenethyl)-2,4,6-trihydroxybenzamide with N-(4-(3,5-dichlorophenoxy)phenethyl)-2,4,6-trihydroxybenzamide.

White solid. MS: m/z 467.8, [M+H]$^+$; $^1$H NMR (500 MHz, d$_6$-DMSO) δ 14.8 (s, 1), 11.4 (s, 1), 10.6 (s, 1), 8.75 (t, J=5.6 Hz, 1), 7.39-7.29 (m, 3), 7.08 (d, J=8.5 Hz, 2), 7.01 (d, J=1.8 Hz, 2), 6.12 (d, J=4.1 Hz, 1), 3.59 (dd, J=13.1, 6.9 Hz, 2), 2.87 (t, J=7.2 Hz, 2). Also noted 4.03 (q, EtOAc), 1.99 (s, EtOAc), 1.24 (s), 1.18 (t, EtOAc).

Example 30: Synthesis of 3,5-dichloro-N-(4-(3,5-dichlorophenoxy)phenethyl)-2,4,6-trihydroxybenzamide (0MTK238

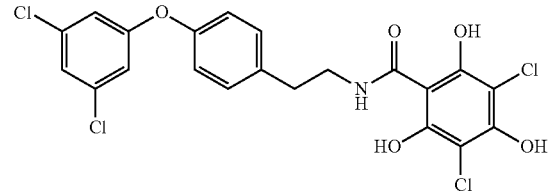 [SMILES: O=C(NCCc1ccc(Oc2cc(Cl)cc(Cl)c2)cc1)c1c(O)c(Cl)c(O)c(Cl)c1O]

0MTK238 was synthesized as described for 0MTK221, but replacing N-(4-chlorophenethyl)-2,4,6-trihydroxybenzamide with N-(4-(3,5-dichlorophenoxy)phenethyl)-2,4,6-trihydroxybenzamide.

White solid. MS: m/z 503.8, [M+H]$^+$; $^1$H NMR (500 MHz, d$_6$-DMSO) δ 13.1 (br s, 2), 10.6 (s, 1), 8.99 (s, 1), 7.40-7.27 (m, 3), 7.08 (d, J=8.5 Hz, 2), 7.01 (d, J=1.8 Hz, 2), 3.61 (dd, J=12.9, 7.0 Hz, 2), 2.89 (t, J=7.1 Hz, 2). Also noted 4.03 (q, EtOAc), 1.99 (s, EtOAc), 1.24 (s), 1.18 (t, EtOAc).

Example 31: Synthesis of 3-chloro-N-(4-(4-fluorophenoxy)phenethyl)-2,4,6-trihydroxybenzamide (0MTK240

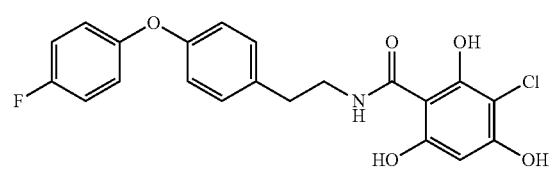 [SMILES: O=C(NCCc1ccc(Oc2ccc(F)cc2)cc1)c1c(O)cc(O)c(Cl)c1O]

0MTK240 was synthesized as described for 0MTK222, but replacing N-(4-chlorophenethyl)-2,4,6-trihydroxybenzamide with N-(4-(4-fluorophenoxy)phenethyl)-2,4,6-trihydroxybenzamide.

White solid. MS: m/z 418.0, [M+H]⁺; ¹H NMR (500 MHz, d₆-DMSO) δ 7.26 (d, J=8.4 Hz, 2), 7.08 (t, J=8.7 Hz, 2), 7.01-6.95 (m, 2), 6.93 (d, J=8.5 Hz, 2), 6.03 (s, 1), 3.63 (t, J=7.0 Hz, 2), 2.89 (t, J=7.0 Hz, 2). Also noted 4.11 (q, EtOAc), 2.03 (s, EtOAc), 1.30 (s), 1.26 (t, EtOAc).

Example 32: Synthesis of N-(4-(3-chlorophenoxy)phenethyl)-2,4,6-trihydroxybenzamide (0MTK256

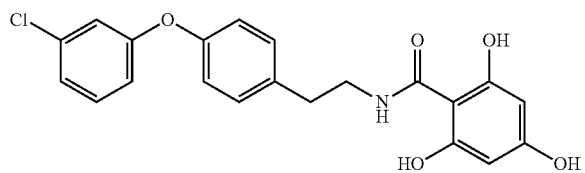 [SMILES: O=C(NCCc1ccc(Oc2cccc(Cl)c2)cc1)c1c(O)cc(O)cc1O]

0MTK256 was synthesized as described for 0MTK180, but replacing (3,5-dichlorophenyl)boronic acid with (3-chlorophenyl)boronic acid.

White solid. MS: m/z 400.0, [M+H]⁺; ¹H NMR (500 MHz, d₆-DMSO) δ 12.6 (br s, 2), 9.89 (s, 1), 8.65 (t, J=5.5 Hz, 1), 7.39 (t, J=8.2 Hz, 1), 7.32 (d, J=8.4 Hz, 2), 7.18 (d, J=7.0 Hz, 1), 7.06-6.99 (m, 3), 6.93 (dd, J=8.3, 2.3 Hz, 1), 5.79 (s, 2), 3.61-3.50 (m, 2), 2.85 (t, J=7.1 Hz, 2); also noted, 4.03 (q, EtOAc), 1.99 (s, EtOAc), 1.18 (t, EtOAc).

Example 33: Synthesis of 2,4,6-trihydroxy-N-(4-(p-tolyloxy)phenethyl)benzamide (0MTK257

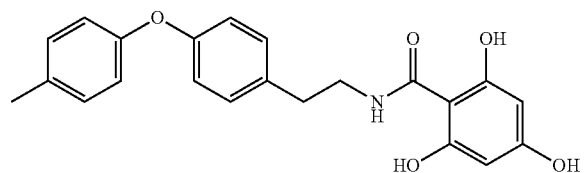 [SMILES: Cc1ccc(Oc2ccc(CCNC(=O)c3c(O)cc(O)cc3O)cc2)cc1]

0MTK257 was synthesized as described for 0MTK180, but replacing (3,5-dichlorophenyl)boronic acid with p-tolylboronic acid.

White solid. MS: m/z 380.0, [M+H]⁺; ¹H NMR (500 MHz, d₆-DMSO) δ 12.6 (s, 2), 9.88 (s, 1), 8.64 (t, J=5.6 Hz, 1), 7.25 (d, J=8.4 Hz, 2), 7.18 (d, J=8.5 Hz, 2), 6.90 (dd, J=8.3, 6.4 Hz, 4), 5.79 (s, 2), 3.53 (dd, J=13.1, 6.8 Hz, 2), 2.81 (t, J=7.1 Hz, 2), 2.29 (s, 3). Also noted 4.03 (q, EtOAc), 1.99 (s, EtOAc), 1.22 (s), 1.18 (t, EtOAc).

Example 34: Synthesis of 2,4,6-trihydroxy-N-(4-(4-methoxyphenoxy)phenethyl)benzamide (0MTK260

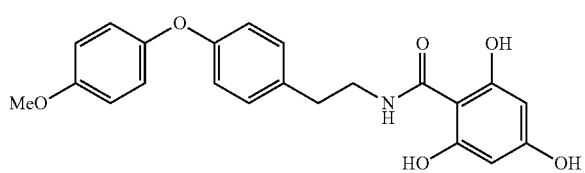 [SMILES: COc1ccc(Oc2ccc(CCNC(=O)c3c(O)cc(O)cc3O)cc2)cc1]

0MTK260 was synthesized as described for 0MTK180, but replacing (3,5-dichlorophenyl)boronic acid with (4-methoxyphenyl)boronic acid.

Brown oil. MS: m/z 396.0, [M+H]P; ¹H NMR (500 MHz, d₆-DMSO) δ 12.6 (br s, 2), 9.88 (s, 1), 8.65 (s, 1), 7.23 (d, J=8.3 Hz, 2), 6.97 (q, J=9.3 Hz, 4), 6.87 (d, J=8.3 Hz, 2), 5.78 (s, 2), 3.75 (s, 3), 3.55-3.48 (m, 2), 2.80 (t, J=7.1 Hz, 2). Also noted peaks at 4.1 (q, EtOAc), 3.3 (s, H2O), 2.1 (s, EtOAc), 1.3 (s), 1.2 (t, EtOAc).

Example 35: Synthesis of 2,4,6-trihydroxy-N-(4-(4-morpholinophenoxy)phenethyl)benzamide (0MTK261

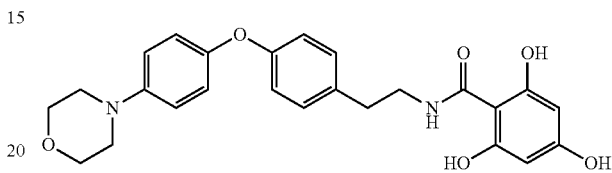

0MTK261 was synthesized as described for 0MTK180, but replacing (3,5-dichlorophenyl)boronic acid with (4-morpholinophenyl)boronic acid.

White solid. MS: m/z 451.0, [M+H]⁺; NMR (500 MHz, d₆-DMSO) δ 12.6 (br s, 2), 9.89 (s, 1), 8.64 (t, J=5.3 Hz, 1), 7.22 (d, J=8.2 Hz, 2), 6.99 (d, J=8.8 Hz, 2), 6.93 (d, J=8.8 Hz, 2), 6.86 (d, J=8.1 Hz, 2), 5.79 (s, 2), 3.78-3.69 (m, 4), 3.56-3.45 (m, 2), 3.13-3.01 (m, 4), 2.80 (t, J=7.2 Hz, 2); also noted, 6.8 (d), 4.3 (br s, H2O), 4.0 (s), 1.2 (s).

Example 36: Synthesis of 2,4,6-trihydroxy-N-(4-(pyrimidin-5-yloxy)phenethyl)benzamide (0MTK262

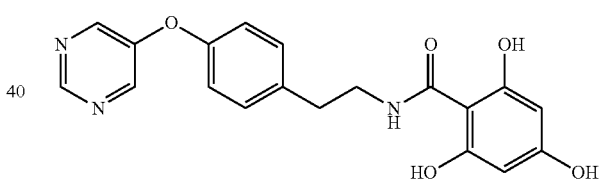

0MTK262 was synthesized as described for 0MTK180, but replacing (3,5-dichlorophenyl)boronic acid with pyrimidin-5-ylboronic acid.

Brown oil. MS: m/z 368.0, [M+H]⁺; ¹H NMR (500 MHz, MeOD) δ 8.91 (s, 1), 8.51 (s, 2), 7.39 (d, J=8.2 Hz, 2), 7.11 (d, J=8.3 Hz, 2), 5.84 (s, 2), 3.65 (t, J=6.9 Hz, 2), 2.94 (t, J=6.9 Hz, 2); also noted, 5.5 (s, DCM), 1.3 (s).

Example 37: Synthesis of 2,4,6-trihydroxy-N-(4-(3-morpholinophenoxy)phenethyl)benzamide (0MTK263

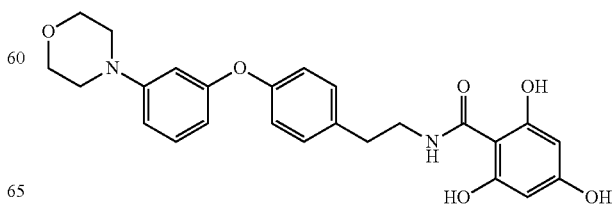

0MTK263 was synthesized as described for 0MTK180, but replacing (3,5-dichlorophenyl)boronic acid with (3-morpholinophenyl)boronic acid.

Beige solid. MS: m/z 451.0, [M+H]% NMR (500 MHz, $d_6$-DMSO) δ 12.6 (br s, 2), 9.87 (s, 1), 8.64 (t, J=5.5 Hz, 1), 7.26 (d, J=8.2 Hz, 2), 7.20 (t, J=8.2 Hz, 1), 6.93 (d, J=8.1 Hz, 2), 6.72 (d, J=8.3 Hz, 1), 6.58 (s, 1), 6.36 (d, J=7.2 Hz, 1), 5.79 (s, 2), 3.75-3.68 (m, 4), 3.57-3.50 (m, 2), 3.13-3.05 (m, 4), 2.82 (t, J=7.1 Hz, 2); also noted, 5.8 (s, DCM), 3.5 (br s, $H_2O$), 1.2 (s).

Example 38: Synthesis of 2,4,6-trihydroxy-N-(4-(pyridin-3-yloxy)phenethyl)benzamide (0MTK2641

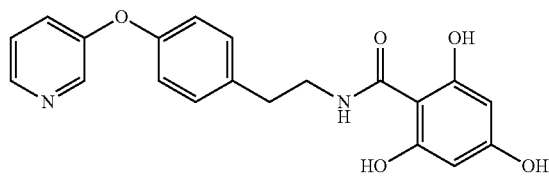 [SMILES: O=C(NCCc1ccc(Oc2cccnc2)cc1)c1c(O)cc(O)cc1O]

0MTK264 was synthesized as described for 0MTK180, but replacing (3,5-dichlorophenyl)boronic acid with pyridin-3-ylboronic acid.

White solid. MS: m/z 367.0, [M+H]$^+$; $^1$H NMR (500 MHz, $d_6$-DMSO) δ 12.6 (br s, 2), 9.86 (s, 1), 8.69 (s, 1), 8.37 (d, J=2.6 Hz, 1), 8.36 (d, J=4.3 Hz, 1), 7.46-7.36 (m, 2), 7.31 (d, J=8.4 Hz, 2), 7.02 (d, J=8.3 Hz, 2), 5.78 (s, 2), 3.55 (dd, J=12.5, 6.5 Hz, 2), 2.84 (t, J=7.1 Hz, 2). Also noted 4.0 (q, EtOAc), 3.3 (s, H2O), 2.0 (s, EtOAc), 1.2 (t, EtOAc).

Example 39: Synthesis of 2,4,6-trihydroxy-N-(4-(pyridin-4-yloxy)phenethyl)benzamide (0MTK265

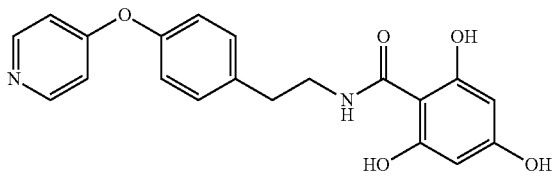 [SMILES: O=C(NCCc1ccc(Oc2ccncc2)cc1)c1c(O)cc(O)cc1O]

0MTK265 was synthesized as described for 0MTK180, but replacing (3,5-dichlorophenyl)boronic acid with pyridin-4-ylboronic acid.

White solid. MS: m/z 367.0, [M+H]$^+$; $^1$H NMR (500 MHz, $d_6$-DMSO) δ 12.6 (br s, 2), 9.87 (s, 1), 8.67 (s, 1), 8.45 (d, J=6.1 Hz, 2), 7.37 (d, J=8.4 Hz, 2), 7.12 (d, J=8.4 Hz, 2), 6.94-6.81 (m, 2), 5.79 (s, 2), 3.62-3.52 (m, 2), 2.88 (t, J=7.1 Hz, 2). Also noted 10.5 (br s), 5.0, 4.0 (q, EtOAc), 3.2 (s), 2.0 (s, EtOAc), 1.3 (t, EtOAc), 2.6, 1.9 (s), 1.2 (s).

Example 40: Synthesis of 2,4,6-trihydroxy-N-(4-(4-(pyridin-4-yl)phenoxy)phenethyl)benzamide (0MTK266

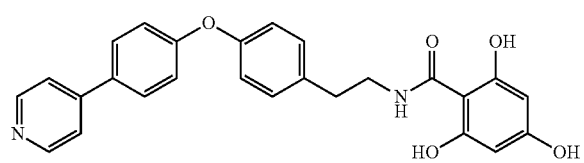 [SMILES: O=C(NCCc1ccc(Oc2ccc(-c3ccncc3)cc2)cc1)c1c(O)cc(O)cc1O]

0MTK266 was synthesized as described for 0MTK180, but replacing (3,5-dichlorophenyl)boronic acid with (4-(pyridin-4-yl)phenyl)boronic acid.

Yellow solid. MS: m/z 443.0, [M+H]% $^1$H NMR (500 MHz, $d_6$-DMSO) δ 12.6 (s, 2), 9.88 (s, 1), 8.66 (s, 1), 8.62 (d, J=5.9 Hz, 2), 7.83 (d, J=8.8 Hz, 2), 7.69 (d, J=6.1 Hz, 2), 7.32 (d, J=8.5 Hz, 2), 7.10 (d, J=8.7 Hz, 2), 7.05 (d, J=8.5 Hz, 2), 5.79 (s, 2), 3.56 (dd, J=12.9, 6.8 Hz, 2), 2.86 (t, J=7.1 Hz, 2). Also noted 10.5 (s), 5.7 (s, DCM), 4.1 (q, MeOH), 3.3 (s, $H_2O$), 3.2 (s), 2.6 (s), 2.0 (s, EtOAc), 1.2 (s), 1.2 (t, EtOAc).

Example 41: Synthesis of 2,4,6-trihydroxy-N-(4-(4-(pyridin-3-yl)phenoxy)phenethyl)benzamide (0MTK267

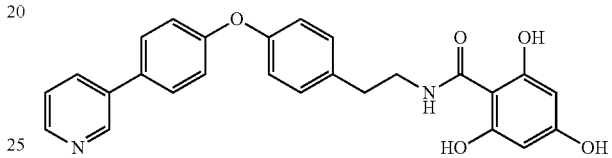

0MTK267 was synthesized as described for 0MTK180, but replacing (3,5-dichlorophenyl)boronic acid with (4-(pyridin-3-yl)phenyl)boronic acid.

White solid. MS: m/z 443.0, [M+H]$^+$; $^1$H NMR (500 MHz, $d_6$-DMSO) b 12.6 (s, 2), 9.88 (s, 1), 8.88 (d, J=2.3 Hz, 1), 8.65 (t, J=5.5 Hz, 1), 8.56 (dd, J=4.7, 1.4 Hz, 1), 8.08-8.02 (m, 1), 7.74 (d, J=8.7 Hz, 2), 7.48 (dd, J=7.9, 4.8 Hz, 1), 7.32 (d, J=8.5 Hz, 2), 7.09 (d, J=8.7 Hz, 2), 7.03 (d, J=8.5 Hz, 2), 5.79 (s, 2), 3.60-3.50 (m, 2), 2.85 (t, J=7.2 Hz, 2). Also noted 10.5 (s), 4.1 (q, MeOH), 3.3 (s, $H_2O$), 3.2 (d, MeOH) 2.6 (s), 1.9 (s).

Example 42: Synthesis of N-(4-(3-(cyclopropylcarbamoyl)phenoxy)phenethyl)-2,4,6-trihydroxybenzamide (0MTK268

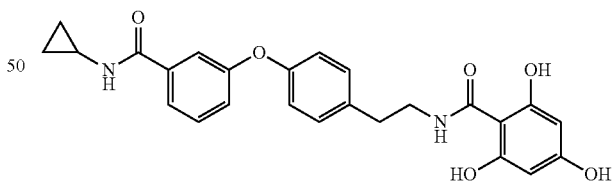

0MTK268 was synthesized as described for 0MTK180, but replacing (3,5-dichlorophenyl)boronic acid with (3-(cyclopropylcarbamoyl)phenyl)boronic acid.

White solid. MS: m/z 449.0, [M+H]$^+$; $^1$H NMR (500 MHz, $d_6$-DMSO) δ 12.6 (s, 2), 9.89 (s, 1), 8.64 (t, J=5.4 Hz, 1), 8.47 (d, J=3.5 Hz, 1), 7.58 (d, J=7.6 Hz, 1), 7.47-7.42 (m, 2), 7.29 (d, J=8.4 Hz, 2), 7.12 (d, J=7.9 Hz, 1), 6.97 (d, J=8.3 Hz, 2), 5.78 (s, 2), 3.54 (dd, J=13.0, 6.6 Hz, 2), 2.83 (t, J=7.4 Hz, 3), 0.69-0.65 (m, 2), 0.55 (t, J=5.3 Hz, 2). Also noted 6.53 (s), 3.33 (s, $H_2O$).

Example 43: Synthesis of 2,4,6-trihydroxy-N-(4-(3-(pyridin-4-yl)phenoxy)phenethyl)benzamide (0MTK269

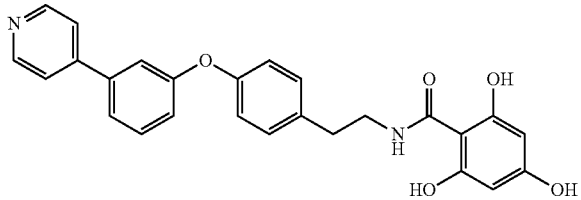 [SMILES: O=C(NCCc1ccc(Oc2cccc(-c3ccncc3)c2)cc1)c1c(O)cc(O)cc1O]

0MTK269 was synthesized as described 0MTK180, but replacing (3,5-dichlorophenyl)boronic acid with (3-(pyridin-4-yl)phenyl)boronic acid.

Light brown solid. MS: m/z 443.0, [M+H]$^+$; $^1$H NMR (500 MHz, d$_6$-DMSO) δ 12.6 (br s, 2), 9.90 (s, 1), 8.82 (br s, 2), 8.65 (t, J=5.6 Hz, 1), 7.99 (s, 2), 7.65 (d, J=7.5 Hz, 1), 7.57 (d, J=8.0 Hz, 1), 7.54 (s, 1), 7.31 (d, J=8.4 Hz, 2), 7.11 (d, J=8.0 Hz, 1), 7.03 (d, J=8.4 Hz, 2), 5.78 (s, 2), 2.84 (t, J=7.1 Hz, 2). Also noted 3.5 (br s), 1.24 (s). 2 protons unaccounted for in the aliphatic region, most likely underneath the 3.5 (br s).

Example 44: Synthesis of 3,5,5-triethyl-N-(4-(4-fluorophenoxy)phenethyl)-2,4-dihydroxy-6-oxocyclohexa-1,3-dienecarboxamide (3RHTK161

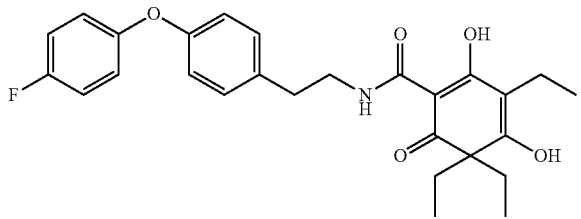 [SMILES: CCC1=C(O)C(CC)(CC)C(=O)C(C(=O)NCCc2ccc(Oc3ccc(F)cc3)cc2)=C1O]

To a solution of N-(4-(4-fluorophenoxy)phenethyl)-2,4-dihydroxy-6-oxocyclohexa-1,3-dienecarboxamide (42.0 mg, 0.110 mmol) in MeOH (1.00 ml), was added 25 w % MeONa in MeOH (0.100 ml, 0.438 mmol) and iodoethane (40.0 µl, 0.497 mmol), and the mixture was stirred overnight at 20° C. The reaction mixture was supplemented with 10% aqueous citric acid (20 ml) and extracted with ethyl acetate (2×40 ml), and the pooled organic extracts were washed with saturated aqueous brine solution (20 ml), dried over anhydrous Na$_2$SO$_4$, filtered, and evaporated under vacuum. The residue was purified by prep-HPLC (C18, buffer A=0.1% TFA-H$_2$O, buffer B=0.1% TFA-Acetonitrile), to afford 3,5,5-triethyl-N-(4-(4-fluorophenoxy)phenethyl)-2,4-dihydroxy-6-oxocyclohexa-1,3-dienecarboxamide (3RHTK161) as a white solid (24.2 mg, 0.0517 mmol, 47% yield).

MS: m/z 468.0, [M+H]$^+$; $^1$H NMR (500 MHz, d$_6$-DMSO) δ (1:1 tautomers) 10.6 (s, 0.5), 10.4 (t, J=5.7 Hz, 0.5), 10.3 (t, J=6.0 Hz, 0.5), 9.90 (s, 0.5), 7.30-7.15 (m, 4), 7.02 (ddd, J=9.1, 7.0, 4.5 Hz, 2), 6.92 (dd, J=10.1, 8.6 Hz, 2), 3.60-3.45 (m, 2), 3.17 (s, 1), 2.83 (q, J=7.3 Hz, 2), 2.37 (dq, J=22.3, 7.4 Hz, 2), 1.93 (dq, J=15.0, 7.5 Hz, 1), 1.85-1.68 (m, 3), 0.96 (t, J=7.3 Hz, 1.5), 0.89 (t, J=7.3 Hz, 1.5), 0.57 (t, J=7.4 Hz, 3), 0.53 (t, J=7.4 Hz, 3); also noted, 3.97 (s), 3.3 (br s, H2O), 2.64 (s), 1.24 (s).

Example 45: Assay of Inhibition of Bacterial RNA Polymerase

Example 45.1: Assay of Inhibition of Escherichia coli RNA Polymerase

Fluorescence-detected RNA polymerase assays with E. coli RNA polymerase were performed by a modification of the procedure of Kuhlman et al., 2004 [Kuhlman, P., Duff, H. & Galant, A. (2004) A fluorescence-based assay for multisubunit DNA-dependent RNA polymerases. Anal. Biochem. 324, 183-190]. Reaction mixtures contained (200): 0-100 nM test salt, 75 nM E. coli RNA polymerase σ$^{70}$ holoenzyme, 20 nM 384 bp DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM MgCl$_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM CaCl$_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC$_{50}$ is defined as the concentration of inhibitor resulting in 50% inhibition of RNA polymerase activity.

Example 45.2: Assay of Inhibition of Staphylococcus aureus RNA Polymerase

Fluorescence-detected RNA polymerase assays with S. aureus RNA polymerase were performed as in Example 2.1, using reaction mixtures containing (20 µl): 0-100 nM test salt, 75 nM S. aureus RNA polymerase core enzyme, 300 nM S. aureus σ$^4$, 20 nM 384 bp DNA fragment containing the bacteriophage T4 N25 promoter, 100 µM ATP, 100 µM GTP, 100 µM UTP, 100 µM CTP, 40 mM Tris-HCl, pH 8.0, 80 mM NaCl, 5 mM MgCl$_2$, 2.5 mM DTT, and 12.7% glycerol. IC$_{50}$ is defined as the concentration of inhibitor resulting in 50% inhibition of RNA polymerase activity.

Data for representative compounds fare provided in Table 1.

TABLE 1

Inhibition of bacterial RNA polymerase

| Compound | RNAP-inhibitory activity E. coli RNAP IC$_{50}$ (µM) | RNAP-inhibitory activity S. aureus RNAP IC$_{50}$ (µM) |
|---|---|---|
| 0MTK107 | 0.40 | 2.0 |
| 0MTK127 | 0.37 | 1.5 |
| 0MTK128 | 0.97 | >100 |
| 0MTK146 | 0.69 | 2.7 |
| 0MTK148 | 0.80 | 3.9 |
| 0MTK149 | 0.14 | 1.5 |
| 0MTK154 | 0.42 | 3.5 |
| 0MTK155 | 0.79 | 8.1 |
| 0MTK156 | 0.82 | 5.5 |
| 0MTK158 | 0.22 | 1.8 |
| 0MTK174 | 0.41 | 14 |
| 0MTK175 | 0.45 | 7.0 |

TABLE 1-continued

Inhibition of bacterial RNA polymerase

| Compound | RNAP-inhibitory activity E. coli RNAP IC$_{50}$ (µM) | RNAP-inhibitory activity S. aureus RNAP IC$_{50}$ (µM) |
|---|---|---|
| 0MTK176 | 0.39 | 12 |
| 0MTK178 | 0.61 | 18 |
| 0MTK180 | 0.83 | 6.6 |
| 0MTK181 | 1.4 | >60 |
| 0MTK183 | 1.7 | 14 |
| 0MTK204 | 7.0 | 8.0 |
| 0MTK207 | 7.4 | 13 |
| 0MTK208 | 7.2 | 5.0 |
| 0MTK221 | 14 | 98 |
| 0MTK222 | 6.8 | 9.0 |
| 0MTK223 | 6.6 | 10 |
| 0MTK224 | 25 | >100 |
| 0MTK230 | 7.7 | 35 |
| 0MTK231 | 8.4 | 31 |
| 0MTK232 | 0.72 | 8.0 |
| 0MTK233 | 4.5 | 23 |
| 0MTK237 | 0.31 | 3.0 |
| 0MTK238 | 0.77 | 3.0 |
| 0MTK240 | 2.1 | 15 |
| 0MTK256 | 0.65 | 10 |
| 0MTK257 | 0.80 | 11 |
| 0MTK260 | 0.78 | 6.2 |
| 0MTK261 | 1.5 | 7.5 |
| 0MTK262 | 1.5 | 7.4 |
| 0MTK263 | 1.3 | 7.1 |
| 0MTK264 | 0.82 | 3.8 |
| 0MTK265 | 1.3 | 6.4 |
| 0MTK266 | 1.2 | 5.1 |
| 0MTK267 | 0.30 | 1.7 |
| 0MTK268 | 0.80 | 2.9 |
| 0MTK269 | 0.70 | 3.0 |
| 3RKHTK161 | 3.3 | 13 |

Example 46: Assay of Inhibition of Growth of *Staphylococcus aureus*

Minimum inhibitory concentrations (MICs for *Staphylococcus aureus* ATCC 12600 were quantified using spiral gradient endpoint assays, essentially as described [Wallace, A. and Corkill, J. (1989) Application of the spiral plating method to study antimicrobial action. *J. Microbiol. Meths.* 10, 303-310; Paton, J., Holt, A., and Bywater, M. (1990) Measurement of MICs of antibacterial agents by spiral gradient endpoint compared with conventional dilution methods. *Int. I Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-100 µg/ml of test salt. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-salt concentration at the streak endpoint was calculated using the program SGE (Spiral Biotech, Inc.), and the MIC was defined as the calculated test-salt concentration at the streak endpoint.

Data for representative compounds are provided in Table 2.

TABLE 2

Inhibition of bacterial growth

| Example | in vitro antibacterial activity S. aureus ATCC12600 MIC (µg/ml) |
|---|---|
| 0MTK107 | >40 |
| 0MTK127 | 20 |
| 0MTK128 | >20 |
| 0MTK146 | 22 |
| 0MTK148 | 19 |
| 0MTK149 | 19 |
| 0MTK154 | 15 |
| 0MTK155 | 8.1 |
| 0MTK156 | 8.3 |
| 0MTK158 | 5.4 |
| 0MTK174 | 8.6 |
| 0MTK175 | 8.6 |
| 0MTK176 | 5.3 |
| 0MTK178 | 7.8 |
| 0MTK180 | 1.8 |
| 0MTK181 | 6.9 |
| 0MTK183 | 6.1 |
| 0MTK204 | 27 |
| 0MTK207 | 19 |
| 0MTK208 | 11 |
| 0MTK221 | >40 |
| 0MTK222 | >40 |
| 0MTK223 | >40 |
| 0MTK224 | >40 |
| 0MTK230 | >40 |
| 0MTK231 | 33 |
| 0MTK232 | 20 |
| 0MTK233 | 6.8 |
| 0MTK237 | 15 |
| 0MTK238 | 3.2 |
| 0MTK240 | >40 |
| 0MTK256 | 9.1 |
| 0MTK257 | 20 |
| 3RKHTK161 | 2.8 |

Example 47. Assay of Antibacterial Efficacy in Mouse Model of *Staphylococcus aureus* Systemic Infection ("Peritonitis Model"

Female Swiss Webster mice (0.18-0.22 kg) were experimentally infected by intraperitoneal administration of 1×10$^7$ colony forming units of methicillin-resistant *Staphylococcus aureus* (MRSA) strain BAA-1707 (USA-400, MW2) in 5% hog gastric mucin. Test compounds in vehicle (5% dimethylacetamide and 4% cremophor EL in 10 mM sodium phosphate, pH 8), positive control (linezolid in vehicle), and negative control (vehicle only), were administered by intravenous injection into a tail vein (200 µl) 0 h post-infection. Identities of test compounds and controls were blinded from personnel performing injections and monitoring survival. The protective dose 50 (PD50) was defined as the test-compound dose resulting in 50% survival at 72 h (calculated using the probit method).

Data for representative compounds are provided in Table 3.

TABLE 3

Antibacterial efficacy in mice: methicillin-resistant *Staphylococcus aureus* (MRSA) peritonitis

| Example | in vivo antibacterial activity mouse MRSA peritonitis ED50 (mg/kg) |
|---|---|
| 0MTK148 | 2.5 |

The data in Table 1 show that certain compounds of this invention potently inhibit bacterial RNA polymerases. The data in Table 1 further show that certain compounds of this invention potently inhibit the both RNA polymerase from the Gram-negative bacterium *Escherichia col* and RNA polymerase from the Gram-positive bacterium *Staphylococcus aureus*. The data in Table 2 show that certain compounds of this invention potently inhibit bacterial growth. The data in Table 3 indicate that certain compounds of this invention potently clear bacterial infection and prevent death in a mammal.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

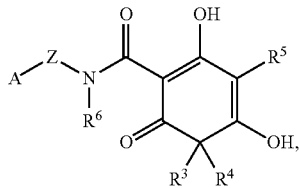

or a tautomer or a salt thereof, wherein:
Z is —C($R^a R^b$)—, —C($R^a R^b$)C($R^c R^d$)—, or —C($R^a R^b$)C($R^c R^d$)C($R^e R^f$)—;
A is selected from the group consisting of:

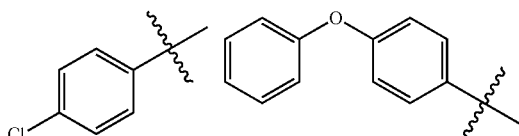

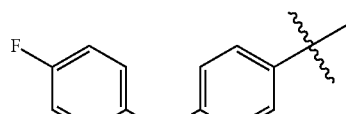

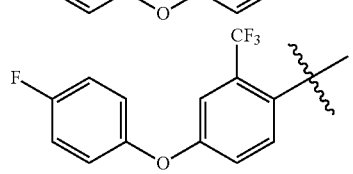

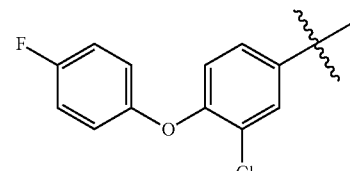

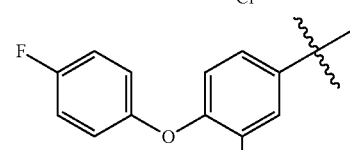

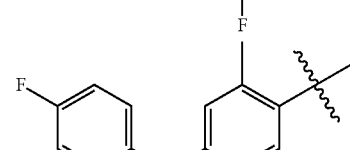

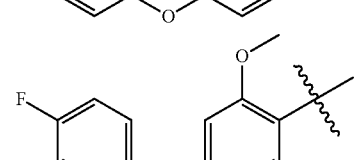

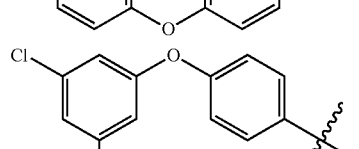

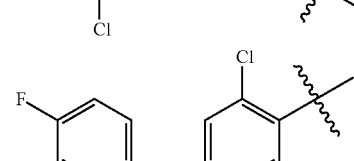

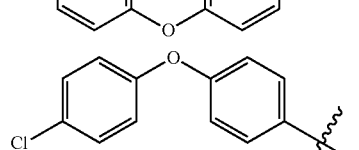

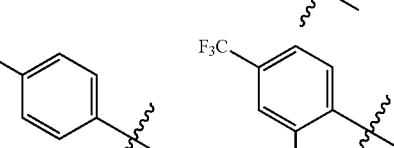

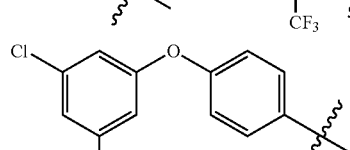

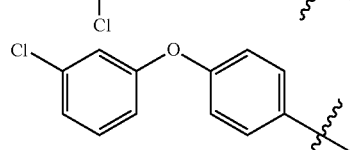

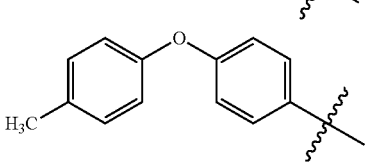

-continued

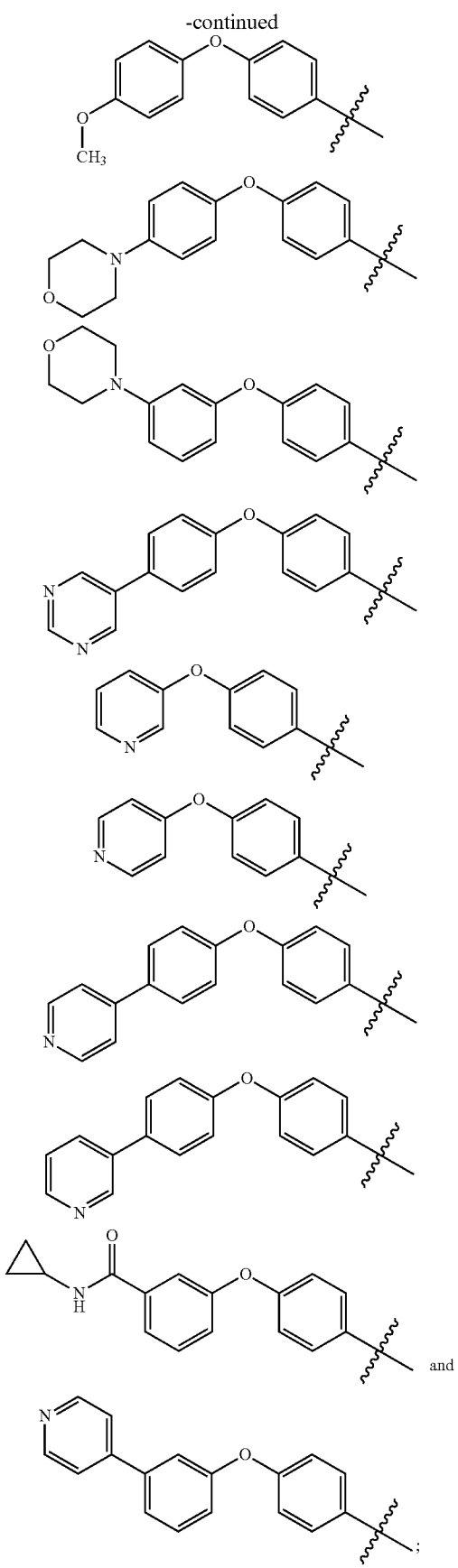

R³ is H, halo, (C₁-C₈)alkyl, or (C₂-C₈)alkenyl, which (C₁-C₈)alkyl, or (C₂-C₈)alkenyl optionally is substituted with one or more of halo, oxo, hydroxy, —CO$_2$R$^r$, —CONR$^u$R$^v$, cyano, —NR$^g$R$^h$R$^i$, sulfonate, fluoromethoxy, difluoromethoxy, trifluoromethoxy, (C₁-C₈)alkyl, (C₂-C₈)alkenyl, (C₁-C₈)alkoxy, aryl, heteroaryl, aryloxy, or heteroaryloxy;

R⁴ is H, halo, (C₁-C₈)alkyl, or (C₂-C₈)alkenyl, which (C₁-C₈)alkyl, or (C₂-C₈)alkenyl optionally is substituted with one or more of halo, oxo, hydroxy, —CO$_2$R$^k$—CONR$^m$R$^n$, cyano, —NR$^g$R$^h$R$^i$, sulfonate, fluoromethoxy, difluoromethoxy, trifluoromethoxy, (C₁-C₈)alkyl, (C₂-C₈)alkenyl, (C₁-C₈)alkoxy, aryl, heteroaryl, aryloxy, or heteroaryloxy;

R⁵ is H, halo, (C₁-C₈)alkyl, or (C₂-C₈)alkenyl, which (C₁-C₈)alkyl, or (C₂-C₈)alkenyl optionally is substituted with one or more of halo, oxo, hydroxy, —CO$_2$R$^p$, —CONR$^r$R$^s$, cyano, —NR$^g$R$^h$R$^i$, sulfonate, fluoromethoxy, difluoromethoxy, trifluoromethoxy, (C₁-C₈)alkyl, (C₂-C₈)alkenyl, (C₁-C₈)alkoxy, aryl, heteroaryl, aryloxy, or heteroaryloxy;

R⁶ is H, (C₁-C₆)alkyl or (C₂-C₆)alkenyl, which (C₁-C₆)alkyl or (C₂-C₆)alkenyl optionally is substituted with halo;

R$^a$, R$^b$, R$^c$, R$^d$, R$^e$, and R$^f$ each independently is H, halo, (C₁-C₆)alkyl, (C₂-C₆)alkenyl, or (C₁-C₆)alkoxy, which (C₁-C₆)alkyl, (C₂-C₆)alkenyl, or (C₁-C₆)alkoxy optionally is substituted with halo; or R$^a$, R$^b$, and the carbon to which they are attached, or R$^c$, R$^d$, and the carbon to which they are attached, or R$^e$, R$^f$, and the carbon to which they are attached, form a cylopropyl ring; or R$^a$ and the carbons to which R$^a$ and R$^c$ are attached, or R$^c$ and the carbons to which R$^c$ and R$^e$ are attached, form a cylopropyl ring;

R$^g$ and R$^h$ each independently is H or (C₁-C₆)alkyl, or R$^g$ and R$^h$, together with the nitrogen to which they are attached, form a morpholino, piperazino, pyrrolidino, or piperidino; and each R$^i$ independently is absent, H, or (C₁-C₆)alkyl, provided that when R$^i$ is H or (C₁-C₆)alkyl and the nitrogen to which R$^i$ is attached is a a positively charged ammonium nitrogen, then the positively charged ammonium nitrogen is associated with a pharmaceutically acceptable counter ion M;

R$^k$ is H or (C₁-C₆)alkyl;

R$^m$ and R$^n$ each independently is H or (C₁-C₆)alkyl that is optionally substituted with one or more of halo;

R$^p$ is H or (C₁-C₆)alkyl that is optionally substituted with one or more of halo;

R$^r$ and R$^s$ each independently is H or (C₁-C₆)alkyl that is optionally substituted with one or more of halo;

R$^t$ is H or (C₁-C₆)alkyl that is optionally substituted with one or more of halo; and R$^u$ and R$^v$ each independently is H or (C₁-C₆)alkyl that is optionally substituted with one or more of halo.

2. A compound of formula II:

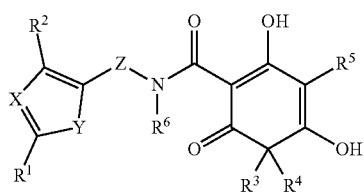

or a tautomer or a salt thereof, wherein:

X and Y are individually carbon, sulfur, oxygen, or nitrogen, wherein at least one of X and Y is other than carbon;

Z is —C($R^a R^b$)—, —C($R^a R^b$)C($R^c R^d$)—, or —C($R^a R^b$)C($R^c R^d$)C($R^e R^f$)—;

$R^1$ is H, halo, ($C_1$-$C_6$)alkyl, ($C_2$-$C_6$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo; or $R^1$ is aryl-($C_1$-$C_6$)alkyl-, aryloxy, or heteroaryloxy, which aryl-($C_1$-$C_6$)alkyl-, aryloxy, or heteroarlyoxy optionally is substituted by one or more of halo, ($C_1$-$C_6$)alkyl, ($C_2$-$C_6$)alkenyl, ($C_1$-$C_6$)alkoxy, aryl, heteroaryl, morpholino, piperazinyl, and —CONR$^y$R$^z$, which ($C_1$-$C_6$)alkyl, ($C_2$-$C_6$)alkenyl, ($C_1$-$C_6$)alkoxy, aryl, heteroaryl, morpholino, or piperazinyl is optionally substituted with halo;

$R^2$ is H, halo, ($C_1$-$C_6$)alkyl, ($C_2$-$C_6$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo;

$R^3$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —CO$_2$R$^t$, —CONR$''$R$^v$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^4$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —CO$_2$R$^k$, —CONR$^m$R$^n$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^5$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —CO$_2$R$^p$, —CONR$^r$R$^s$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^6$ is H, ($C_1$-$C_6$)alkyl or ($C_2$-$C_6$)alkenyl, which ($C_1$-$C_6$)alkyl or ($C_2$-$C_6$)alkenyl optionally is substituted with halo;

$R^a$, $R^b$, $R^c$, $R^d$, $R^e$, and $R^f$ each independently is H, halo, ($C_1$-$C_6$)alkyl, ($C_2$-$C_6$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo; or $R^a$, $R^b$, and the carbon to which they are attached, or $R^c$, $R^d$, and the carbon to which they are attached, or $R^e$, $R^f$, and the carbon to which they are attached, form a cylopropyl ring; or $R^a$ and the carbons to which $R^a$ and $R^c$ are attached, or $R^c$ and the carbons to which $R^c$ and $R^e$ are attached, form a cylopropyl ring;

$R^g$ and $R^h$ each independently is H or ($C_1$-$C_6$)alkyl, or $R^g$ and $R^h$, together with the nitrogen to which they are attached, form a morpholino, piperazino, pyrrolidino, or piperidino; and each $R^i$ independently is absent, H, or ($C_1$-$C_6$)alkyl, provided that when $R^i$ is H or ($C_1$-$C_6$)alkyl and the nitrogen to which $R^i$ is attached is a a positively charged ammonium nitrogen, then the positively charged ammonium nitrogen is associated with a pharmaceutically acceptable counter ion M;

$R^k$ is H or ($C_1$-$C_6$)alkyl;

$R^m$ and $R^n$ each independently is H or ($C_1$-$C_6$)alkyl that is optionally substituted with one or more of halo;

$R^p$ is H or ($C_1$-$C_6$)alkyl that is optionally substituted with one or more of halo;

$R^r$ and $R^s$ each independently is H or ($C_1$-$C_6$)alkyl that is optionally substituted with one or more of halo;

$R^t$ is H or ($C_1$-$C_6$)alkyl that is optionally substituted with one or more of halo;

$R^u$ and $R^v$ each independently is H or ($C_1$-$C_6$)alkyl that is optionally substituted with one or more of halo;

and $R^y$ and $R^z$ each independently is H or ($C_1$-$C_6$)alkyl that is optionally substituted with one or more of halo.

3. A compound selected from the group consisting of:

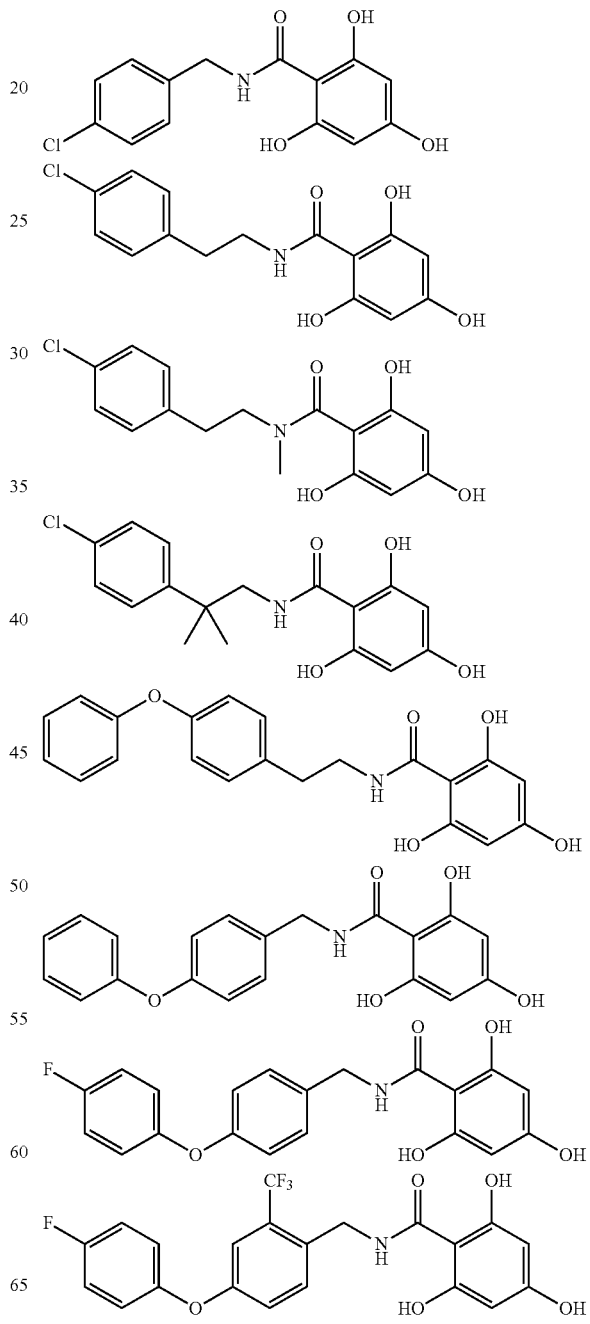

-continued
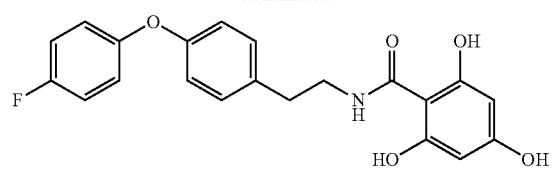
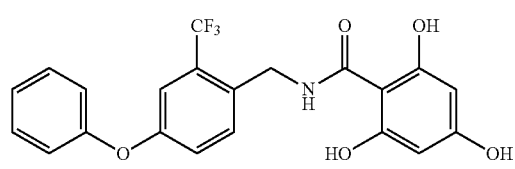
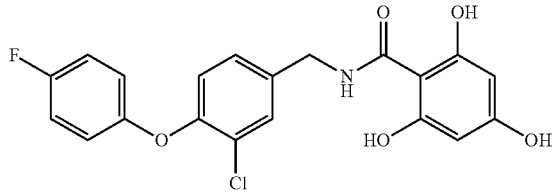
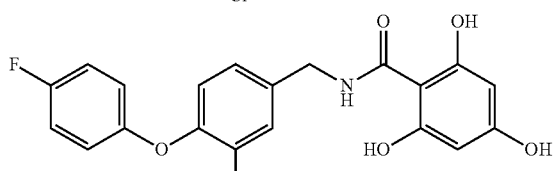
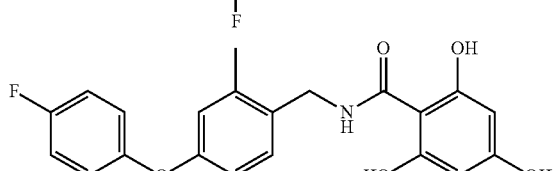
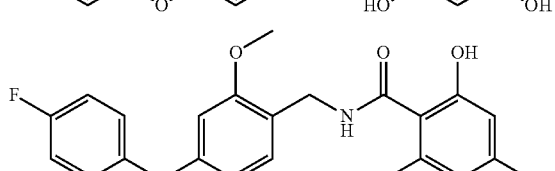
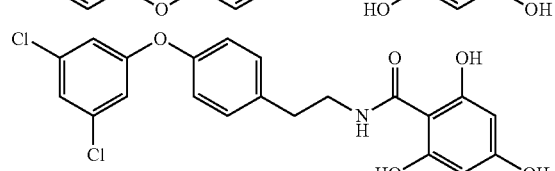
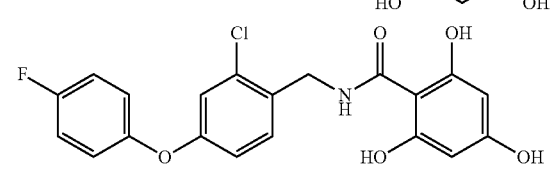
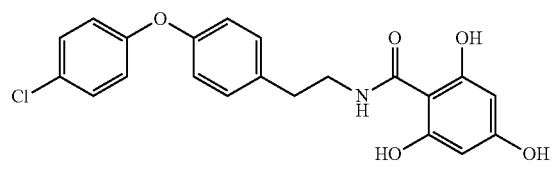
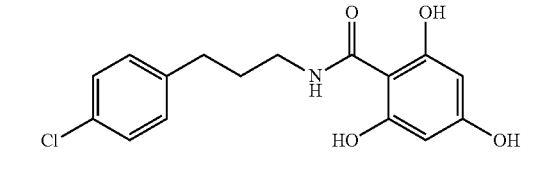
-continued
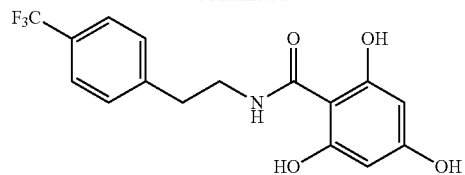
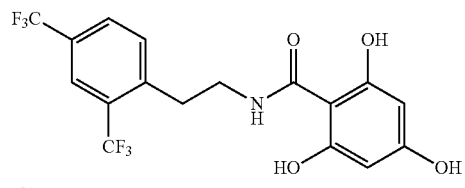
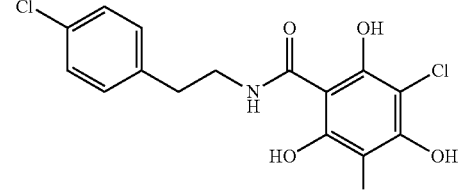
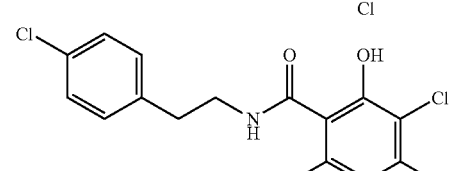
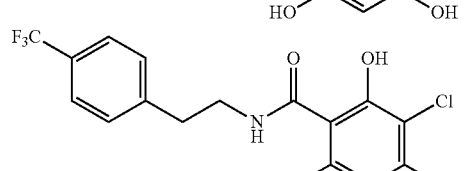
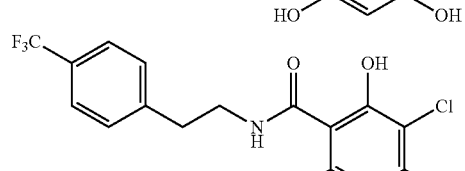
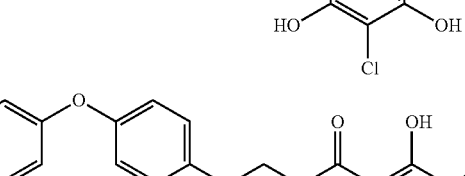
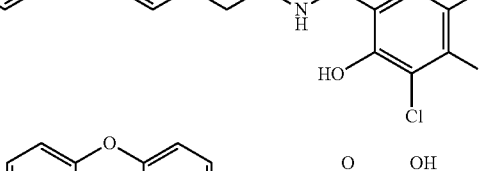
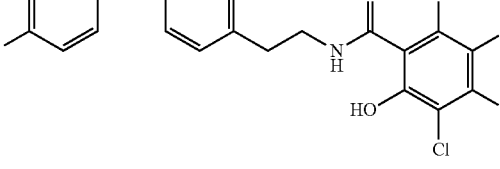
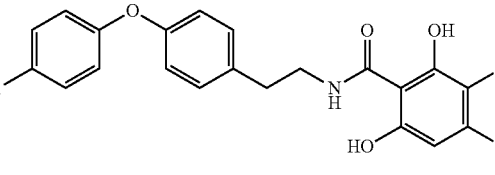

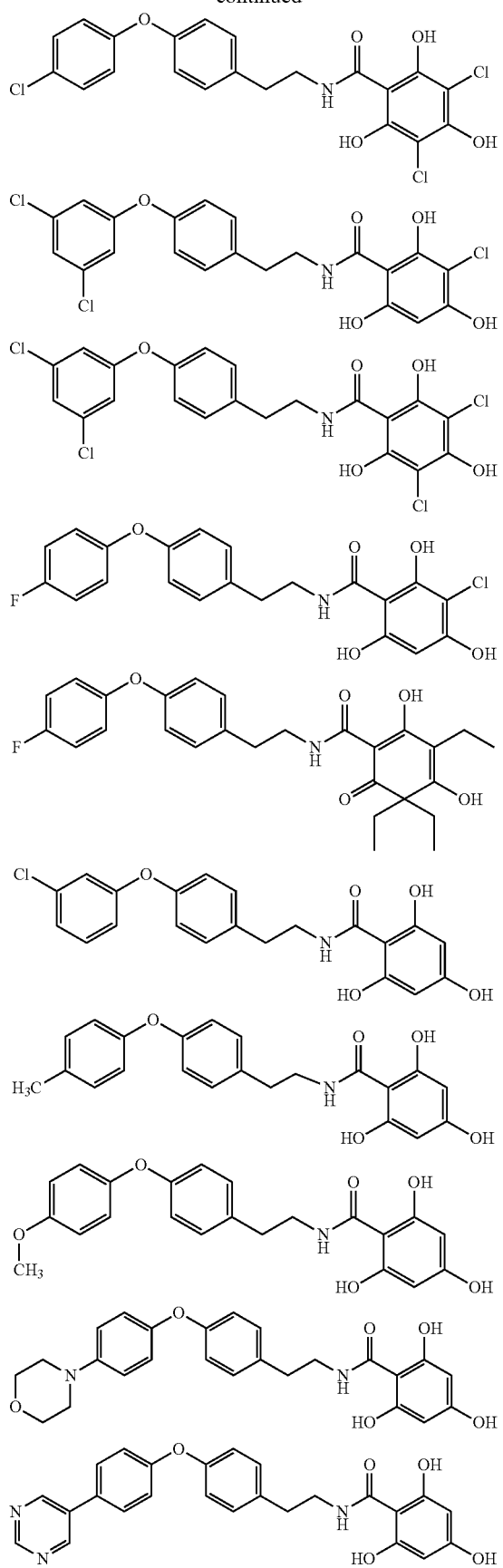
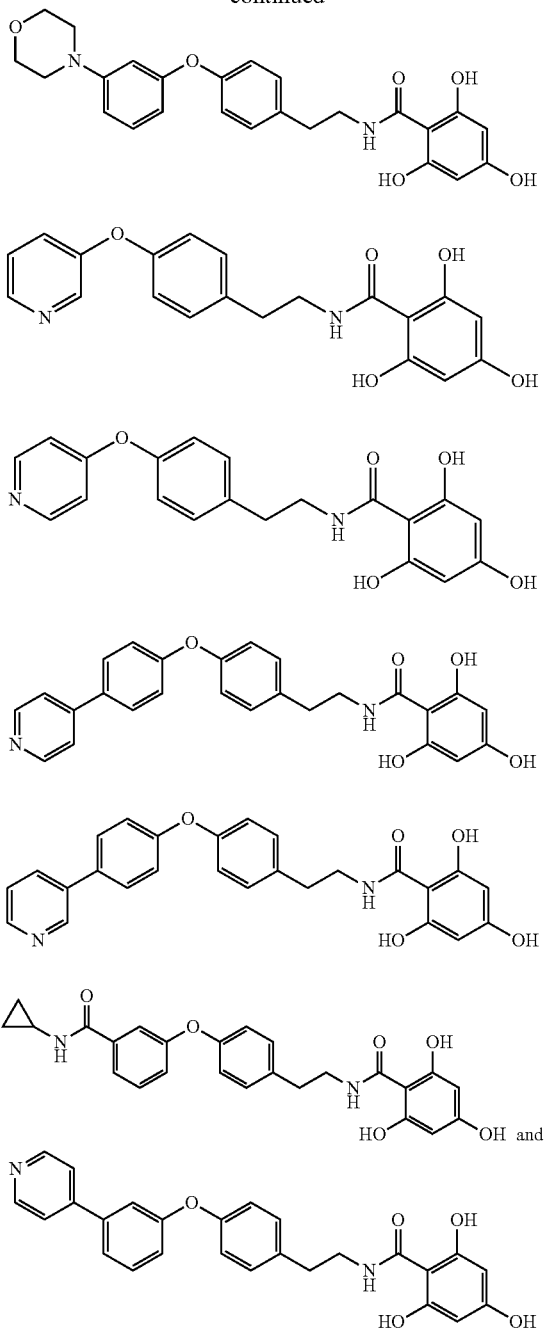
or tautomer or salt thereof.
4. A pharmaceutical composition comprising a compound of formula I or II:
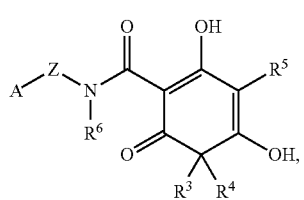
I -continued

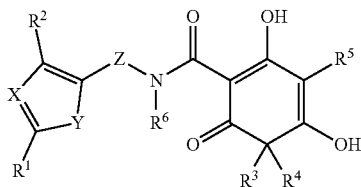

or a tautomer or a pharmaceutically acceptable salt thereof, wherein:

X and Y are individually carbon, sulfur, oxygen, or nitrogen, wherein at least one of X and Y is other than carbon;

Z is —C($R^a R^b$)—, —C($R^a R^b$)C($R^c R^d$)—, or —C($R^a R^b$)C($R^c R^d$)C($R^e R^f$)—;

A is a phenyl ring that is substituted with one or more groups independently selected from the group consisting of halo, ($C_1$-$C_6$)alkyl, ($C_2$-$C_6$)alkenyl, ($C_1$-$C_6$)alkoxy, aryl-($C_1$-$C_6$)alkyl-, aryloxy, and heteroaryloxy, wherein any ($C_1$-$C_6$)alkyl, and ($C_1$-$C_8$)alkoxy of A is substituted by one or more halo, wherein any ($C_2$-$C_6$)alkenyl of A is optionally substituted by one or more halo, and wherein any aryl-($C_1$-$C_6$)alkyl-, aryloxy, and heteroaryloxy of A is substituted by one or more groups independently selected from the group consisting of halo, ($C_1$-$C_6$)alkyl, ($C_2$-$C_6$)alkenyl, ($C_1$-$C_6$)alkoxy, aryl, heteroaryl, morpholino, piperazinyl, and —CONR$^w$R$^x$, which ($C_1$-$C_6$)alkyl, ($C_2$-$C_6$)alkenyl, ($C_1$-$C_6$)alkoxy, aryl, heteroaryl, morpholino, or piperazinyl optionally is substituted with halo;

$R^1$ is H, halo, ($C_1$-$C_6$)alkyl, ($C_2$-$C_6$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo; or $R^1$ is aryl-($C_1$-$C_6$)alkyl-, aryloxy, or heteroaryloxy, which aryl-($C_1$-$C_6$)alkyl-, aryloxy, or heteroarlyoxy optionally is substituted by one or more of halo, ($C_1$-$C_6$)alkyl, ($C_2$-$C_6$)alkenyl, ($C_1$-$C_6$)alkoxy, aryl, heteroaryl, morpholino, piperazinyl, and —CONR$^y$R$^z$, which ($C_1$-$C_6$)alkyl, ($C_2$-$C_6$)alkenyl, ($C_1$-$C_6$)alkoxy, aryl, heteroaryl, morpholino, or piperazinyl is optionally substituted with halo;

$R^2$ is H, halo, ($C_1$-$C_6$)alkyl, ($C_2$-$C_6$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo;

$R^3$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —CO$_2$R$^t$, —CONR$^u$R$^v$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^4$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —CO$_2$R$^k$, —CONR$^m$R$^n$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^5$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —CO$_2$R$^p$, —CONR$^m$R$^n$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^6$ is H, ($C_1$-$C_6$)alkyl or ($C_2$-$C_6$)alkenyl, which ($C_1$-$C_6$)alkyl or ($C_2$-$C_6$)alkenyl optionally is substituted with halo;

$R^a$, $R^b$, $R^c$, $R^d$, $R^e$, and $R^f$ each independently is H, halo, ($C_1$-$C_6$)alkyl, ($C_2$-$C_6$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo; or $R^a$, $R^b$, and the carbon to which they are attached, or $R^c$, $R^d$, and the carbon to which they are attached, or $R^e$, $R^f$, and the carbon to which they are attached, form a cylopropyl ring; or $R^a$ and the carbons to which $R^a$ and $R^c$ are attached, or $R^c$ and the carbons to which $R^c$ and $R^e$ are attached, form a cylopropyl ring;

$R^g$ and $R^h$ each independently is H or ($C_1$-$C_6$)alkyl, or $R^g$ and $R^h$, together with the nitrogen to which they are attached, form a morpholino, piperazino, pyrrolidino, or piperidino; and each $R^i$ independently is absent, H, or ($C_1$-$C_6$)alkyl, provided that when $R^i$ is H or ($C_1$-$C_6$)alkyl and the nitrogen to which $R^i$ is attached is a a positively charged ammonium nitrogen, then the positively charged ammonium nitrogen is associated with a pharmaceutically acceptable counter ion M;

$R^k$ is H or ($C_1$-$C_6$)alkyl;

$R^m$ and $R^n$ each independently is H or ($C_1$-$C_6$)alkyl that is substituted with one or more of halo;

$R^p$ is H or ($C_1$-$C_6$)alkyl that is substituted with one or more of halo;

$R^r$ and $R^s$ each independently is H or ($C_1$-$C_6$)alkyl that is substituted with one or more of halo;

$R^t$ is H or ($C_1$-$C_6$)alkyl that is substituted with one or more of halo;

$R^u$ and $R^v$ each independently is H or ($C_1$-$C_6$)alkyl that is substituted with one or more of halo;

$R^w$ and $R^x$ each independently is H or ($C_1$-$C_6$)alkyl that is substituted with one or more of halo; and $R^y$ and $R^z$ each independently is H or ($C_1$-$C_6$)alkyl that is substituted with one or more of halo and a pharmaceutically acceptable carrier.

5. A method of inhibiting a bacterial RNA polymerase, comprising contacting a bacterial RNA polymerase with compound of formula I or II:

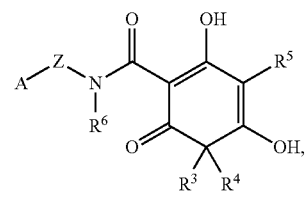

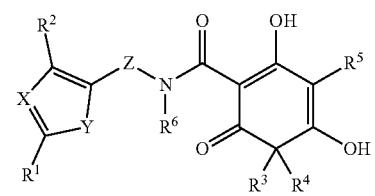

or a tautomer or a salt thereof, wherein:

X and Y are individually carbon, sulfur, oxygen, or nitrogen, wherein at least one of X and Y is other than carbon;

Z is —C($R^aR^b$)—, —C($R^aR^b$)C($R^cR^d$)—, or —C($R^aR^b$)C($R^cR^d$)C($R^eR^f$)—;

A is a phenyl ring that is substituted with one or more groups independently selected from the group consisting of halo, ($C_1$-$C_6$)alkyl, ($C_2$-$C_6$)alkenyl, ($C_1$-$C_6$) alkoxy, aryl-($C_1$-$C_6$)alkyl-, aryloxy, and heteroaryloxy, wherein any ($C_1$-$C_6$)alkyl, ($C_2$-$C_6$)alkenyl, and ($C_1$-$C_6$) alkoxy of A is optionally substituted by one or more halo, and wherein any aryl-($C_1$-$C_6$)alkyl-, aryloxy, and heteroaryloxy of A is optionally substituted by one or more groups independently selected from the group consisting of halo, ($C_1$-$C_6$)alkyl, ($C_2$-$C_6$)alkenyl, ($C_1$-$C_6$)alkoxy, aryl, heteroaryl, morpholino, piperazinyl, and —CONR$^w$R$^x$, which ($C_1$-$C_6$)alkyl, ($C_2$-$C_6$)alkenyl, ($C_1$-$C_6$)alkoxy, aryl, heteroaryl, morpholino, or piperazinyl optionally is substituted with halo;

$R^1$ is H, halo, ($C_1$-$C_6$)alkyl, ($C_2$-$C_6$)alkenyl, or ($C_1$-$C_6$) alkoxy, which ($C_1$-$C_6$)alkyl, ($C_2$-$C_6$)alkenyl, or ($C_1$-$C_6$) alkoxy optionally is substituted with halo; or $R^1$ is aryl-($C_1$-$C_6$)alkyl-, aryloxy, or heteroaryloxy, which aryl-($C_1$-$C_6$)alkyl-, aryloxy, or heteroarlyoxy optionally is substituted by one or more of halo, ($C_1$-$C_6$)alkyl, ($C_2$-$C_6$)alkenyl, ($C_1$-$C_6$)alkoxy, aryl, heteroaryl, morpholino, piperazinyl, and —CONR$^y$R$^z$, which ($C_1$-$C_6$) alkyl, ($C_2$-$C_6$)alkenyl, ($C_1$-$C_6$)alkoxy, aryl, heteroaryl, morpholino, or piperazinyl is optionally substituted with halo;

$R^2$ is H, halo, ($C_1$-$C_6$)alkyl, ($C_2$-$C_6$)alkenyl, or ($C_1$-$C_6$) alkoxy, which ($C_1$-$C_6$)alkyl, ($C_2$-$C_6$)alkenyl, or ($C_1$-$C_6$) alkoxy optionally is substituted with halo;

$R^3$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —$CO_2R^t$, —CONR$^u$R$^v$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^4$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —$CO_2R^t$, —CONR$^u$R$^v$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$)alkoxy, aryl, heteroaryl, aryloxy, or heteroaryloxy;

$R^5$ is H, halo, ($C_1$-$C_8$)alkyl, or ($C_2$-$C_8$)alkenyl, which ($C_1$-$C_8$)alkyl, or ($C_2$-$C_8$)alkenyl optionally is substituted with one or more of halo, oxo, hydroxy, —$CO_2R^k$, —CONR$^m$R$^n$, cyano, —NR$^g$R$^h$R$^i$, sulfonate, fluoromethoxy, difluoromethoxy, trifluoromethoxy, ($C_1$-$C_8$)alkyl, ($C_2$-$C_8$)alkenyl, ($C_1$-$C_8$) alkoxy, aryl, heteroaryl, aryloxy, or heteroaryloxy;

$R^6$ is H, ($C_1$-$C_6$)alkyl or ($C_2$-$C_6$)alkenyl, which ($C_1$-$C_6$) alkyl or ($C_2$-$C_6$)alkenyl optionally is substituted with halo;

$R^a$, $R^b$, $R^c$, $R^d$, $R^e$, and $R^f$ each independently is H, halo, ($C_1$-$C_6$)alkyl, ($C_2$-$C_8$)alkenyl, or ($C_1$-$C_6$)alkoxy, which ($C_1$-$C_6$)alkyl, ($C_2$-$C_6$)alkenyl, or ($C_1$-$C_6$)alkoxy optionally is substituted with halo; or $R^a$, $R^b$, and the carbon to which they are attached, or $R^c$, $R^d$, and the carbon to which they are attached, or $R^e$, $R^f$, and the carbon to which they are attached, form a cylopropyl ring; or $R^a$ and the carbons to which $R^a$ and $R^c$ are attached, or $R^c$ and the carbons to which $R^c$ and $R^e$ are attached, form a cyloproypl ring;

$R^g$ and $R^h$ each independently is H or ($C_1$-$C_6$)alkyl, or $R^g$ and $R^h$, together with the nitrogen to which they are attached, form a morpholino, piperazino, pyrrolidino, or piperidino; and each $R^i$ independently is absent, H, or ($C_1$-$C_6$)alkyl, provided that when $R^i$ is H or ($C_1$-$C_6$) alkyl and the nitrogen to which $R^i$ is attached is a a positively charged ammonium nitrogen, then the positively charged ammonium nitrogen is associated with a pharmaceutically acceptable counter ion M;

$R^k$ is H or ($C_1$-$C_6$)alkyl;

$R^m$ and $R^n$ each independently is H or ($C_1$-$C_6$)alkyl that is substituted with one or more of halo;

$R^p$ is H or ($C_1$-$C_6$)alkyl that is substituted with one or more of halo;

$R^r$ and $R^s$ each independently is H or ($C_1$-$C_6$)alkyl that is substituted with one or more of halo;

$R^t$ is H or ($C_1$-$C_6$)alkyl that is substituted with one or more of halo;

$R^u$ and $R^v$ each independently is H or ($C_1$-$C_6$)alkyl that is substituted with one or more of halo;

$R^w$ and $R^x$ each independently is H or ($C_1$-$C_6$)alkyl that is substituted with one or more of halo; and $R^y$ and $R^z$ each independently is H or ($C_1$-$C_6$)alkyl that is substituted with one or more of halo.

6. A method of treating a bacterial infection in a mammal, comprising administering to the mammal a therapeutically effective amount of compound of formula I or II:

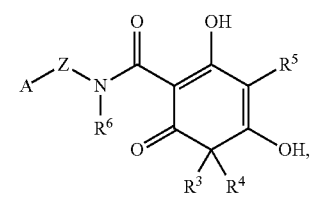

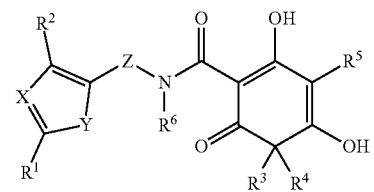

or a tautomer or a pharmaceutically acceptable salt thereof, wherein:

X and Y are individually carbon, sulfur, oxygen, or nitrogen, wherein at least one of X and Y is other than carbon;

Z is —C($R^aR^b$)—, —C($R^aR^b$)C($R^cR^d$)—, or —C($R^aR^b$)C($R^cR^d$)C($R^eR^f$)—;

A is a phenyl ring that is substituted with one or more groups independently selected from the group consisting of halo, ($C_1$-$C_6$)alkyl, ($C_2$-$C_6$)alkenyl, ($C_1$-$C_6$) alkoxy, aryl-($C_1$-$C_6$)alkyl-, aryloxy, and heteroaryloxy, wherein any ($C_1$-$C_6$)alkyl, ($C_2$-$C_6$)alkenyl, and ($C_1$-$C_6$) alkoxy of A is optionally substituted by one or more halo, and wherein any aryl-($C_1$-$C_6$)alkyl-, aryloxy, and heteroaryloxy of A is optionally substituted by one or more groups independently selected from the group consisting of halo, ($C_1$-$C_6$)alkyl, ($C_2$-$C_6$)alkenyl, ($C_1$-$C_6$)alkoxy, aryl, heteroaryl, morpholino, piperazinyl, and —CONR$^w$R$^x$, which ($C_1$-$C_6$)alkyl, ($C_2$-$C_6$)alkenyl, ($C_1$-$C_6$)alkoxy, aryl, heteroaryl, morpholino, or piperazinyl optionally is substituted with halo;

$R^1$ is H, halo, ($C_1$-$C_6$)alkyl, ($C_2$-$C_6$)alkenyl, or ($C_1$-$C_6$) alkoxy, which ($C_1$-$C_6$)alkyl, ($C_2$-$C_6$)alkenyl, or ($C_1$-$C_6$) alkoxy optionally is substituted with halo; or $R^1$ is aryl-$(C_1-C_6)$alkyl-, aryloxy, or heteroaryloxy, which aryl-$(C_1-C_6)$alkyl-, aryloxy, or heteroarlyoxy optionally is substituted by one or more of halo, $(C_1-C_6)$alkyl, $(C_2-C_6)$alkenyl, $(C_1-C_6)$alkoxy, aryl, heteroaryl, morpholino, piperazinyl, and —CONR$^y$R$^z$, which $(C_1-C_6)$alkyl, $(C_2-C_6)$alkenyl, $(C_1-C_6)$alkoxy, aryl, heteroaryl, morpholino, or piperazinyl is optionally substituted with halo;

R$^2$ is H, halo, $(C_1-C_6)$alkyl, $(C_2-C_6)$alkenyl, or $(C_1-C_6)$alkoxy, which $(C_1-C_6)$alkyl, $(C_2-C_6)$alkenyl, or $(C_1-C_6)$alkoxy optionally is substituted with halo;

R$^3$ is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, —CO$_2$R$^t$, —CONR$^u$R$^v$, cyano, —NR$^g$R$^h$R$^i$, sulfonate, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, or heteroaryloxy;

R$^4$ is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, —CO$_2$R$^k$, —CONR$^m$R$^n$, cyano, —NR$^g$R$^h$R$^i$, sulfonate, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, or heteroaryloxy;

R$^5$ is H, halo, $(C_1-C_8)$alkyl, or $(C_2-C_8)$alkenyl, which $(C_1-C_8)$alkyl, or $(C_2-C_8)$alkenyl optionally is substituted with one or more of halo, oxo, hydroxy, —CO$_2$R$^p$, —CONR$^r$R$^s$, cyano, —NR$^g$R$^h$R$^i$, sulfonate, fluoromethoxy, difluoromethoxy, trifluoromethoxy, $(C_1-C_8)$alkyl, $(C_2-C_8)$alkenyl, $(C_1-C_8)$alkoxy, aryl, heteroaryl, aryloxy, or heteroaryloxy;

R$^6$ is H, $(C_1-C_6)$alkyl or $(C_2-C_6)$alkenyl, which $(C_1-C_6)$alkyl or $(C_2-C_6)$alkenyl optionally is substituted with halo;

R$^a$, R$^b$, R$^c$, R$^d$, R$^e$, and R$^f$ each independently is H, halo, $(C_1-C_6)$alkyl, $(C_2-C_8)$alkenyl, or $(C_1-C_6)$alkoxy, which $(C_1-C_6)$alkyl, $(C_2-C_6)$alkenyl, or $(C_1-C_6)$alkoxy optionally is substituted with halo; or R$^a$, R$^b$, and the carbon to which they are attached, or R$^c$, R$^d$, and the carbon to which they are attached, or R$^e$, R$^f$, and the carbon to which they are attached, form a cylopropyl ring; or R$^a$ and the carbons to which R$^a$ and R$^c$ are attached, or R$^c$ and the carbons to which R$^c$ and R$^e$ are attached, form a cylopropyl ring;

R$^g$ and R$^h$ each independently is H or $(C_1-C_6)$alkyl, or R$^g$ and R$^h$, together with the nitrogen to which they are attached, form a morpholino, piperazino, pyrrolidino, or piperidino; and each R$^i$ independently is absent, H, or $(C_1-C_6)$alkyl, provided that when R$^i$ is H or $(C_1-C_6)$alkyl and the nitrogen to which R$^i$ is attached is a a positively charged ammonium nitrogen, then the positively charged ammonium nitrogen is associated with a pharmaceutically acceptable counter ion M;

R$^k$ is H or $(C_1-C_6)$alkyl;

R$^m$ and R$^n$ each independently is H or $(C_1-C_6)$alkyl that is substituted with one or more of halo;

R$^p$ is H or $(C_1-C_6)$alkyl that is substituted with one or more of halo;

R$^r$ and R$^s$ each independently is H or $(C_1-C_6)$alkyl that is substituted with one or more of halo;

R$^t$ is H or $(C_1-C_6)$alkyl that is substituted with one or more of halo;

R$^u$ and R$^v$ each independently is H or $(C_1-C_6)$alkyl that is substituted with one or more of halo;

R$^w$ and R$^x$ each independently is H or $(C_1-C_6)$alkyl that is substituted with one or more of halo; and R$^y$ and R$^z$ each independently is H or $(C_1-C_6)$alkyl that is substituted with one or more of halo.

* * * * *

UNITED STATES PATENT AND TRADEMARK OFFICE
CERTIFICATE OF CORRECTION

PATENT NO. : 11,572,337 B2
APPLICATION NO. : 16/978135
DATED : February 7, 2023
INVENTOR(S) : Richard H. Ebright et al.

It is certified that error appears in the above-identified patent and that said Letters Patent is hereby corrected as shown below:

In the Claims

Column 47, Line 41, Claim 5, please delete "-CONR$^u$R$^v$" and insert -- -CONR$^m$R$^n$ --; and Column 47, Line 48, Claim 5, please delete "-CONR$^m$R$^n$" and insert -- -CONR$^r$R$^s$ -- therefor.

Signed and Sealed this
Thirteenth Day of February, 2024

Katherine Kelly Vidal
*Director of the United States Patent and Trademark Office*